(12) United States Patent
Song et al.

(10) Patent No.: US 11,495,111 B2
(45) Date of Patent: Nov. 8, 2022

(54) INDOOR OCCUPANCY ESTIMATION, TRAJECTORY TRACKING AND EVENT MONITORING AND TRACKING SYSTEM

(71) Applicant: University of Georgia Research Foundation, Inc., Athens, GA (US)

(72) Inventors: WenZhan Song, Alpharetta, GA (US); Fangyu Li, Athens, GA (US); Jose Clemente, Bogart, GA (US)

(73) Assignee: UNIVERSITY OF GEORGIA RESEARCH FOUNDATION, INC, Athens, GA (US)

( * ) Notice: Subject to any disclaimer, the term of this patent is extended or adjusted under 35 U.S.C. 154(b) by 0 days.

(21) Appl. No.: 17/423,337

(22) PCT Filed: Feb. 6, 2020

(86) PCT No.: PCT/US2020/017034
§ 371 (c)(1),
(2) Date: Jul. 15, 2021

(87) PCT Pub. No.: WO2020/163611
PCT Pub. Date: Aug. 13, 2020

(65) Prior Publication Data
US 2022/0101709 A1    Mar. 31, 2022

Related U.S. Application Data

(60) Provisional application No. 62/801,786, filed on Feb. 6, 2019.

(51) Int. Cl.
*G08B 21/04* (2006.01)
*A61B 5/00* (2006.01)
(Continued)

(52) U.S. Cl.
CPC .......... *G08B 21/043* (2013.01); *A61B 5/0002* (2013.01); *A61B 5/1117* (2013.01);
(Continued)

(58) Field of Classification Search
CPC .................................................. G08B 21/043
See application file for complete search history.

(56) References Cited

U.S. PATENT DOCUMENTS 6,752,766 B2    6/2004  Kowallik et al.
2004/0267147 A1   12/2004  Sullivan
(Continued)

FOREIGN PATENT DOCUMENTS

WO    2018/165485 A1    9/2018

OTHER PUBLICATIONS

Alessio Agneessens, Igor Bisio, Fabio Lavagetto, Mario Marchese, and Andrea Sciarrone. 2010. Speaker count application for smartphone platforms. In Wireless Pervasive Computing (ISWPC), 2010 5th IEEE International Symposium on. IEEE, 361-366.
(Continued)

*Primary Examiner* — Travis R Runnings
(74) *Attorney, Agent, or Firm* — Thomas | Horstemeyer

(57) ABSTRACT

The present disclosure relates to a monitoring system configured to monitor the activities of individuals without having to keep the surrounding area under the surveillance of a camera thereby maintaining the privacy of the individual. In particular, the monitoring system includes a network of sensitive sensor units that are installed onto indoor flooring to record human footstep induced vibrations. The data collected from the sensors can then be processed to identify individual occupants, determine the number of occupants, estimate the location of footsteps, and track the trajectory of each occupant. The extracted trajectory information can be used to assess an occupant's personal activity
(Continued)

and social interaction, which can then be used to analyze the individual's physical and psychological health.

20 Claims, 13 Drawing Sheets

(51) Int. Cl.
  *A61B 5/11* (2006.01)
  *G01V 1/00* (2006.01)
  *G08B 7/06* (2006.01)
  *G08B 25/10* (2006.01)

(52) U.S. Cl.
  CPC .............. *A61B 5/6887* (2013.01); *A61B 5/742* (2013.01); *A61B 5/7405* (2013.01); *A61B 5/746* (2013.01); *A61B 5/7475* (2013.01); *G01V 1/001* (2013.01); *G08B 7/06* (2013.01); *G08B 21/0461* (2013.01); *G08B 25/10* (2013.01); *A61B 2562/046* (2013.01)

(56) References Cited

U.S. PATENT DOCUMENTS

| | | | |
|---|---|---|---|
| 2005/0124864 A1 | 6/2005 | Mack et al. | |
| 2006/0171570 A1* | 8/2006 | Brendley | G08B 13/10 340/5.52 |
| 2009/0054792 A1 | 2/2009 | Sato et al. | |
| 2009/0177323 A1* | 7/2009 | Ziegler | G05D 1/0274 901/1 |
| 2010/0016685 A1 | 1/2010 | Muehlsteff et al. | |
| 2012/0132211 A1 | 5/2012 | Halperin et al. | |
| 2012/0262294 A1* | 10/2012 | Nikolovski | G08B 21/043 340/565 |
| 2015/0141772 A1* | 5/2015 | LeBoeuf | G16H 40/63 600/595 |
| 2017/0112671 A1* | 4/2017 | Goldstein | H04R 25/554 |

OTHER PUBLICATIONS

Petre Anghelescu, Gabriel V. Iana, and Ionut Tramandan. 2015. Human footstep detection using seismic sensors. In Electronics, Computers and Artificial Intelligence (ECAI), 2015 7th International Conference on. IEEE, AE-1.
Wenqiang Chen, Maoning Guan, Lu Wang, Rukhsana Ruby, and Kaishun Wu. 2017. FLoc: Device-free passive indoor localization in complex environments. In Communications (ICC), 2017 IEEE International Conference on. IEEE, 1-6.
Diane J. Cook, Aaron Crandall, Geetika Singla, and Brian Thomas. 2010. Detection of social interaction in smart spaces. Cybernetics and Systems: An International Journal 41, 2 (2010), 90-104.
Sylvain Durand and Jacques Froment. 2001. Artifact free signal denoising with wavelets. In Acoustics, Speech, and Signal Processing, 2001. Proceedings. (ICASSP'01). 2001 IEEE International Conference on, vol. 6. IEEE, 3685-3688.
Alexander Ekimov and James M. Sabatier. 2006. Vibration and sound signatures of human footsteps in buildings. The Journal of the Acoustical Society of America 118, 3 (2006), 2021-768.
Varick L. Erickson and Alberto E. Cerpa. 2010. Occupancy based demand response HVAC control strategy. In Proceedings of the 2nd ACM Workshop on Embedded Sensing Systems for Energy-Efficiency in Building. ACM, 7-12.
Martin Ester, Hans-Peter Kriegel, Jörg Sander, Xiaowei Xu, and Others. 1996. A density-based algorithm for discovering clusters in large spatial databases with noise. In Kdd, vol. 96. 226-231.
Ananth N. Iyer, Uchechukwu O. Ofoegbu, Robert E. Yantorno, and Stanley Wenndt. 2006. Speaker Modeling in Conversational Speech with Application to Speaker-Count. In Proc. ICSLP.
Simon J. Julier and Jeffrey K. Uhlmann. 1997. New extension of the Kalman filter to nonlinear systems. In Signal processing, sensor fusion, and target recognition VI, vol. 3068. International Society for Optics and Photonics, 182-194.
Angie King. 2012. Online k-means clustering of nonstationary data. Prediction Project Report (2012), 1-9.
Swarun Kumar, Stephanie Gil, Dina Katabi, and Daniela Rus. 2014. Accurate indoor localization with zero start-up cost. In Proceedings of the 20th annual international conference on Mobile computing and networking. ACM, 483-494.
Heyoung Lee, Jung W. Park, and Abdelsalam S. Helal. 2009. Estimation of indoor physical activity level based on footstep vibration signal measured by MEMS accelerometer in smart home environments. In Mobile Entity Localization and Tracking in GPS-less Environments. Springer, 148-162.
Fangyu Li, Jamie Rich, Kurt J. Marfurt, and Huailai Zhou. 2014. Automatic event detection on noisy microseismograms. In SEG Technical Program Expanded Abstracts 2014. Society of Exploration Geophysicists, 2363-2367.
Fangyu Li and WenZhan Song. 2017. Automatic arrival identification system for real-time microseismic event location. In SEG Technical Program Expanded Abstracts 2017, Society E. of Geophysicists (Ed.). 2934-2939.
Mostafa Mirshekari, Shijia Pan, Pei Zhang, and Hae Y. Noh. 2016. Characterizing wave propagation to improve indoor step-level person localization using floor vibration. In Sensors and Smart Structures Technologies for Civil, Mechanical, and Aerospace Systems 2016, vol. 9803. International Society for Optics and Photonics, 980305.
Nori Nakata and Roel Snieder. 2013. Monitoring a building using deconvolution interferometry. II: Ambient-vibration analysis. Bulletin of the Seismological Society of America 104, 1 (2013), 204-213.
Uchechukwu O. Ofoegbu, Ananth N. Iyer, Robert E. Yantorno, and Brett Y. Smolenski. 2006. A speaker count system for telephone conversations. In Intelligent Signal Processing and Communications, 2006. ISPACS'06. International Symposium on. IEEE, 331-334.
Shijia Pan, Kent Lyons, Mostafa Mirshekari, Hae Y. Noh, and Pei Zhang. 2016a. Multiple Pedestrian Tracking through Ambient Structural Vibration Sensing. In Proceedings of the 14th ACM Conference on Embedded Network Sensor Systems CD-ROM. ACM, 366-367.
Shijia Pan, Mostafa Mirshekari, Hae Y. Noh, and Pei Zhang. 2015a. Structural sensing system with networked dynamic sensing configuration. In Proceedings of the 14th International Conference on Information Processing in Sensor Networks. ACM, 344-345.
Shijia Pan, Mostafa Mirshekari, Pei Zhang, and Hae Y. Noh. 2016b. Occupant traffic estimation through structural vibration sensing. In Sensors and Smart Structures Technologies for Civil, Mechanical, and Aerospace Systems 2016, vol. 9803. International Society for Optics and Photonics, 980306.
Shijia Pan, Ningning Wang, Yuqiu Qian, Irem Velibeyoglu, Hae Y. Noh, and Pei Zhang. 2015b. Indoor person Identification through footstep induced structural vibration. In Proceedings of the 16th International Workshop on Mobile Computing Systems and Applications. ACM, 81-86.
Shijia Pan, Tong Yu, Mostafa Mirshekari, Jonathon Fagert, Amelie Bonde, Ole J. Mengshoel, Hae Y. Noh, and Pei Zhang. 2017. FootprintID: Indoor Pedestrian Identification through Ambient Structural Vibration Sensing. Proceedings of the ACM on Interactive, Mobile, Wearable and Ubiquitous Technologies 1, 3 (2017), 89.
Jeffrey D. Poston. 2018. ILoViT: Indoor Localization via Vibration Tracking. Ph.D. DisseilaLion. Virginia Tech.
Pei Zhang, Hae Y. Noh, P. A. N. Shijia, Ningning Wang, Amelie Bonde, and Moustafa Mirshekari. 2018. Indoor Identification of individuals through footstep induced structural vibration. U.S. Appl. No. 15/544,928.
Aleš Povalač and Jir'i Šebesta. 2010. Phase of arrival ranging method for UHF RFID tags using instantaneous frequency measurement. In ICECom, 2010 Conference Proceedings. IEEE, 1-4.
Sankar Rangarajan, Assegid Kidane, Gang Qian, Stjepan Rajko, and David Birchfield. 2007. The design of a pressure sensing floor for movement based human computer interaction. In European Conference on Smart Sensing and Context. Springer, 46-61.

(56) References Cited

OTHER PUBLICATIONS

James M. Sabatier and Alexander E. Ekimov. 2008. A review of human signatures in urban environments using seismic and acoustic methods. InTechnologies for Homeland Security, 2008 IEEE Conference on. IEEE, 215-220.

Roel Snieder and Erdal Safak. 2006. Extracting the building response using seismic interferometry: Theory and application to the Millikan Library in Pasadena, California. Bulletin of the Seismological Society of America 96, 2 (2006), 586-598.

Fabian-Robert Stöter, Soumitro Chakrabarty, Bernd Edler, and Emanuël A. P. Habets. 2017. Classification vs. Regression in Supervised Learning for Single Channel Speaker Count Estimation. arXiv preprint arXiv:1712.04555 (2017).

Xinyao Tang, Ming-Chun Huang, and Soumyajit Mandal. 2017. An âAl Internet of EarsâAl for crowd-aware smart buildings based on sparse sensor networks. In SENSORS, 2017 IEEE. IEEE, 1-3.

Steven R. Taylor, Stephen J. Arrowsmith, and Dale N. Anderson. 2010. Detection of short time transients from spectrograms using scan statistics. Bulletin of the Seismological Society of America 100, 5A(2010), 1940-1951.

Robert Tibshirani, Guenther Walther, and Trevor Hastie. 2001. Estimating the number of clusters in a data set via the gap statistic. Journal of the Royal Statistical Society: Series B (Statistical Methodology) 63, 2 (2001), 411-423.

Chong-Yaw Wee and Raveendran Paramesran. 2007. Measure of image sharpness using eigenvalues. Information Sciences 177, 12 (2007), 2533-2552.

Joe Wong, Lejia Han, J. Bancroft, and R. Stewart. 2009. Automatic time picking of first arrivals on noisy microseismic data CSEG. 0 0.2 0.4 0.6 0.8 1, 1.2 (2009), 1-1.

Jie Xiong and Kyle Jamieson. 2013. ArrayTrack: a fine-grained indoor location system. Usenix.

Faheem Zafari, Ioannis Papapanagiotou, and Konstantinos Christidis. 2016. Microlocation for internet-of-things-equipped smart buildings. IEEE Internet of Things Journal 3, 1 (2016), 96-112.

PCT Search Report in related, co-ending PCT Application No. PCT/US2020/016019, dated Apr. 21, 2020.

R. Nisha Aurora, Susheel P. Patil, and Naresh M. Pun-jabi, "Portable sleep monitoring for diagnosing sleep apnea in hospitalized patients with heart failure," Chest, 2018.

Weihai Sunfull Geophysical Exploration Equipment Co.,Ltd, "Geophone, 3-Component," http://www. sunfull.com/content/?148. html.

Wen-Zhan Song, Renjie Huang, Mingsen Xu, Behrooz A. Shirazi, and Richard LaHusen, "Design and deployment of sensor network for real-time high-fidelity volcano monitoring," IEEE Transactions on Parallel and Distributed Systems, vol. 21, No. 11, pp. 1658-1674, 2010.

WenZhan Song, Lei Shi, Goutham Kamath, Yao Xie, Zhigang Peng, and Others, "Real-time in-situ seis-mic imaging: Overview and case study," in 2015 SEG Annual Meeting. Society of Exploration Geophysicists, 2015.

Fangyu Li and WenZhan Song, "Automatic arrival identification system for real-time microseismic event location," in SEG Technical Program Expanded Abstracts 2017, Society E. of Geophysicists, Ed., 2017, pp. 2934-2939.

Norimitsu Nakata, Roel Snieder, Takeshi Tsuji, Ken Lamer, and Toshifumi Matsuoka, "Shear wave imaging from traffic noise using seismic interferometry by cross-coherence Shear wave imaging from traffic noise," Geophysics, vol. 76, No. 6, pp. SA97-SA106, 2011.

Shijia Pan, Ningning Wang, Yuqiu Qian, Irem Velibeyo-glu, Hae Y. Noh, and Pei Zhang, "Indoor person identifi-cation through footstep induced structural vibration," in Proceedings of the 16th International Workshop on Mo-bile Computing Systems and Applications. ACM, 2015, pp. 81-86.

Zhenhua Jia, Musaab Alaziz, Xiang Chi, Richard E. Howard, Yanyong Zhang, Pei Zhang, Wade Trappe, Anand Sivasubramaniam, and Ning An, "HB-phone: a bed-mounted geophone-based heart-beat monitoring sys-tem," in Information Processing in Sensor Networks (IPSN), 2016 15th ACM/IEEE International Conference on. IEEE, 2016, pp. 1-12.

Musaab Alaziz, Zhenhua Jia, Jian Liu, Richard Howard, Yingying Chen, and Yanyong Zhang, "Motion scale: A body motion monitoring system using bed-mounted wireless load cells," in Connected Health: Applications, Systems and Engineering Technologies (CHASE), 2016 IEEE First International Conference on. IEEE, 2016, pp. 183-192.

Zhenhua Jia, Amelie Bonde, Sugang Li, Chenren Xu, Jingxian Wang, Yanyong Zhang, Richard E. Howard, and Pei Zhang, "Monitoring a person's heart rate and respiratory rate on a shared bed using geophones," 2017.

Haizhao Yang, "Multiresolution mode decomposition for adaptive time series analysis," arXiv preprint arXiv:1709.06880, 2017.

Norden E. Huang, Zheng Shen, Steven R. Long, Manli C. Wu, Hsing H. Shih, Quanan Zheng, Nai-Chyuan Yen, Chi C. Tung, and Henry H. Liu, "The empirical mode decomposition and the hilbert spectrum for nonlinear and non-stationary time series analysis," in Proceedings of the Royal Society of London A: mathematical, physical and engineering sciences. The Royal Society, 1998, vol. 454, pp. 903-995.

Hau-Tieng Wu, Yi-Hsin Chan, Yu-Ting Lin, and Yung-Hsin Yeh, "Using synchrosqueezing transform to dis-cover breathing dynamics from ECG signals," Applied and Computational Harmonic Analysis, vol. 36, No. 2, pp. 354-359, 2014.

Haizhao Yang, "Synchrosqueezed wave packet trans-forms and diffeomorphism based spectral analysis for 1D general mode decompositions," Applied and Computational Harmonic Analysis, vol. 39, No. 1, pp. 33-66, 2015.

Ingrid Daubechies, Jianfeng Lu, and Hau-Tieng Wu, "Synchrosqueezed wavelet transforms: An empirical mode decomposition-like tool," Applied and computational harmonic analysis, vol. 30, No. 2, pp. 243-261, 2011.

Yang Yang, Zhigang Chu, Linbang Shen, Guoli Ping, and Zhongming Xu, "Fast fourier-based deconvolution for three-dimensional acoustic source identification with solid spherical arrays," Mechanical Systems and Signal Processing, vol. 107, pp. 183-201, Jul. 2018.

PCT Search Report in co-pending related PCT Application No. PCT/US2020/016019, dated Apr. 21, 2020.

PCT Search Report in co-pending, related PCT Application No. PCT/US2020/017034, dated May 11, 2020.

PCT International Search Report in co-pending, related PCT Application No. PCT/US2020/017034, dated May 11, 2020.

Pan, Shijia, et al., "Area Occupancy Counting through Sparse Structural Vibration Sensing", Communication Challenges in the IoT, IEEE Pervasive Computing, Jan.-Mar. 2019, pp. 28-37.

European Partial Supplementary Search Report in co-pending, related EP Application No. 20753145.0, dated Sep. 5, 2022.

Li, Fangyu, et al., "Non-Instrusive and Non-Contact Sleep Monitoring With Seismometer", Center for Cyber-Physical Systems, University of Georgia, IEEE, GlobalSIP, 2018, pp. 449-453.

Extended European Search Report in related, co-pending EP Application No. 20748468.4, dated Sep. 8, 2022.

* cited by examiner

INDOOR OCCUPANCY ESTIMATION, TRAJECTORY TRACKING AND EVENT MONITORING AND TRACKING SYSTEM

CROSS REFERENCE TO RELATED APPLICATIONS

This application is the 35 U.S.C. § 371 national stage application of PCT Application No. PCT/US2020/017034, filed Feb. 6, 2020 which claims priority to, and the benefit of, U.S. provisional application entitled "INDOOR OCCUPANCY ESTIMATION, TRAJECTORY TRACKING AND EVENT MONITORING AND TRACKING SYSTEM" having Ser. No. 62/801,786, filed on Feb. 6, 2019, all which are hereby incorporated by reference in their entireties.

BACKGROUND

Human footsteps induce the floor vibrations. A seismometer is a sensor that can sense floor vibrations. Traditionally, indoor sensing systems use vision, radio frequency (RF), mobile, and acoustic systems to track the movement of individual. Some traditional sensing systems further require an individual to identify themselves which can be an intrusion of privacy.

BRIEF DESCRIPTION OF THE DRAWINGS

The foregoing will be apparent from the following more particular description of example embodiments of the present disclosure, as illustrated in the accompanying drawings in which like reference characters refer to the same parts throughout the different views. The drawings are not necessarily to scale, emphasis instead being placed upon illustrating embodiments of the present disclosure.

SUMMARY

Figure 1:
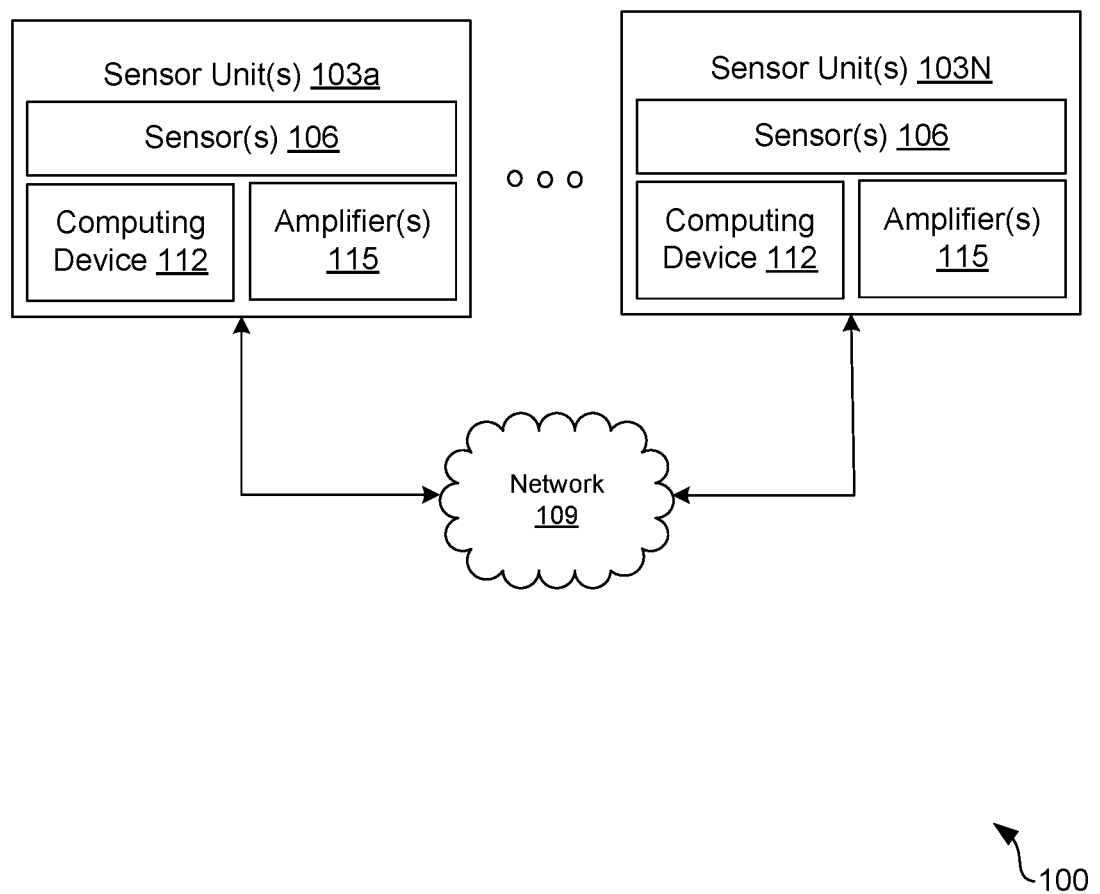
FIG. 1 illustrates an example of a seismic monitoring system according to various embodiments of the present disclosure.

Aspects of the present disclosure are related to monitoring the activities of individuals without having to keep the surrounding area under the surveillance of a camera thereby maintaining the privacy of the individual. In particular, a network of sensitive sensor units can are installed onto indoor flooring to record human footstep induced vibrations. The data collected from the sensors can then be processed to identify individual occupants, determine the number of occupants, estimate the location of footsteps, and track the trajectory of each occupant.

In one aspect, among others, a monitoring system for monitoring activity in a predefined area. The monitoring system includes a network of sensor units arranged on a floor of the predefined area. The individual sensor units of the network of sensor units can includes a sensor, a computing device in data communication with the sensor, and at least one application executable in the computing device. The application can cause the computing device to at least receive sensor data from the sensor, isolate footstep vibrations from the sensor, communicate with at least one other sensor unit in the network of sensor units to obtain neighbor sensor data, and determine at least one of: a number of subjects moving in the predefined area, a trajectory for at least one subject, or a location of the at least one subject based at least in part on the footstep vibrations and the neighbor sensor data. The sensor data can include vibrations associated with one or more subjects moving on the floor.

In various aspects, the sensor includes a seismometer. In various aspects, the network of sensor units are in data communication via a wireless network. In various aspects, isolating the footstep vibrations further comprises identifying one or more footstep signatures in time domain and frequency domain. In various aspects, determining the number of subjects moving in the predefined area further comprises clustering one or more footstep features from the sensor data with one or more footstep features from the neighbor sensor data. In various aspects, the application can further cause the at least one computing device to at least detect an event based at least in part on the footstep vibrations. In various aspects, the event comprises a fall of a particular subject. In various aspects, the application can cause the at least one computing device to at least generate an alert in response to the detected event. In various aspects, the alert is at least one of an auditory or visual alert. In various aspects, the computing device is in communication with a smart device configured to communicate with a third party, and generating the alert further comprises instructing the smart device to send a communication with the third party.

In another aspect, among others, a method for monitoring activity in a predefined area, comprises obtaining, via a computing device of a sensor unit positioned on a floor of the predefined area, sensor data from a sensor of the sensor unit, the sensor data being associated with one or more subjects moving on the floor; isolating, via the computing device, footstep vibrations from the sensor data based at least in part on wavelet denoising; determining, via the computing device, a location of a subject based at least in part on one or more signature features in the footstep vibrations and data received from at least one other sensor unit; and determining, via the computing device, a trajectory of the subject based at least in part on the location of the subject.

In various aspects, the method further comprises estimating, via the computing device, a number of occupants in the predefined area. In various aspects, the sensor comprises a seismometer. In various aspects, the method further comprises further comprising generating, via the computing device, a user interface comprising at least one of: a trajectory tracking, a number of detected footsteps, a number of detected events, a fall down location, a number of detected falls, a time associated with a last detected event, or a time associated with a last detected fall. In various aspects, the method further comprises rendering, via the computing device, the user interface on a display associated with the computing device; and updating, via the computing device, the user interface periodically. In various aspects, the method further comprises detecting, via the computing device, an event of the subject. In various aspects, the event comprises a fall down event. In various aspects, detecting the event is based at least in part on the footstep vibrations. In various aspects, the method further comprises generating, via the computing device, an alert in response to the detected event. In various aspects, the computing device is in communication with a smart device configured to communicate with a third party, and generating the alert comprises instructing the smart device to send a communication with the third party.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

DETAILED DESCRIPTION

The present disclosure relates to a monitoring system configured to monitor the activities of individuals without having to keep the surrounding area under the surveillance of a camera thereby maintaining the privacy of the individual. In particular, the monitoring system of the present disclosure uses a network of sensitive seismometer units that are installed onto indoor flooring to record human footstep induced vibrations. The data collected from the sensors can then be processed to identify individual occupants, determine the number of occupants, estimate the location of footsteps, and track the trajectory of each occupant. The extracted trajectory information can be used to assess an occupant's personal activity and social interaction, which can then be used to analyze the individual's physical and psychological health.

FIG. 1 illustrates an example of a smart monitoring system 100 according to various embodiments of the present disclosure. The smart monitoring system 100 can comprise a plurality of distributed sensor units 103 (e.g., 103a . . . 103N) which are in data communication with one another via a network 106. The network 109 includes, for example, the Internet, intranets, extranets, wide area networks (WANs), local area networks (LANs), wired networks, wireless networks, cable networks, satellite networks, or other suitable networks, etc., or any combination of two or more such networks.

The distributed sensor units 106 can comprise a sensor 109, a computing device 112, and an amplifier 115, and/or other components as can be appreciated. The sensor 109 is configured to obtain both vertical and horizontal vibrations. For example, the sensor 109 can comprise a seismometer and/or any other type of sensor as can be appreciated. The sensor 109 is configured to collect sensor data and communicate with the computing device 112. The amplifiers 109 are configured to facilitate detection.

The computing device 103 can comprise any type of computing device comprising a processor and a memory. Various applications and/or other functionality may be executed in the computing device 103 according to various embodiments. The components executed on the computing device 103, for example, include a seismic tracking application 118 (FIG. 25), a warning module 121 (FIG. 25), and other applications, services, processes, systems, engines, or functionality not discussed in detail herein. Although shown as being part of the sensor unit 103 in FIG. 1, in some examples, the system can comprises a separate computing device 103 that is in communication with the different sensor units 103 in the network 109. As such, the computing device 103 can collect the data from the different sensor units 103 in the network 109 and analyze the data to detect events, such as, for example, a fall down of a subject in a defined area.

The seismic tracking application 118 is executed to collect and store data, process data analytics, communicate with other units, and provide raw and processed data to the visualization tool. For example, the seismic tracking application 118 can collect and process data associated with a given sensor 106 and/or other sensors 106 in the network 109. In some embodiments, the seismic tracking application 118 can generate one or more user interfaces 124 (FIG. 24) that include the raw and processed data that is rendered by a display device (not shown) via the visualization tool. The one or user interfaces 124 that can be updated in real-time. The warning module 118 is executed to generate an alert in an instance in which a particular event is detected. In some embodiments, the warning module 118 is implemented as part of the computing device 103 of the seismic monitoring system 100. For example, the warning module 118 can comprise an application executable in the computing device 103. In other embodiments, the warning module 118 can be separate from the computing device 103 and can be data communication with the computing device 103 over the network 112.

According to various embodiments, the sensors 106 are in data communication with the computing device 1112 via a wired or wireless connection, as can be appreciated. The sensor units 106 can collect sensor data and transmit the collected data to the computing device 103 for analysis. Noise that is generated by appliances in the surrounding area, such as air conditioning, can also generate vibrations. As such, the seismic tracking application 115 can be configured to remove this noise from the collected data by applying wavelet denoising technique which uses relative threshold instead of the traditional fixed threshold.

After denoising, the seismic tracking application 115 can isolate the footstep vibrations are isolated. According to various embodiments, the number of occupants walking in the tested parameter over a given period of time can be computed from the extracted data by employing clustering technique. Single footstep features and gait features can also be inferred based on the different vibration signatures from distinct walking styles. Accordingly, the seismic tracking application 115 can identify individuals according to specific footstep features.

Since global positioning system (GPS) results in lower accuracy inside a building and because the sensor units 103 may be placed too close to one another, a new mechanism for estimating location is disclosed. This mechanism is called phase constrained angle of arrival (PAoA), and combines the Angle of Arrival (AoA) and Phase of Arrival (PoA) methods to maximize accuracy of footsteps localization. Based on the location of footsteps, the path taken by the individual can be traced.

According to various embodiments of the present disclosure, the smart monitoring system 100 can monitor an individual or multiple individuals in one setting. Each individual, without being tagged for identification purposes, can walk in random patterns and by employing machine learning, the location of the footsteps and the path taken by the individuals can be identified. This information, in turn, can be used to monitor analyze the physical health and social interactions of the individuals.

In some embodiments, the seismic monitoring system 100 can detect an event and comprise a warning module 118 configured to generate an alert in an instance in which a particular event is detected. A detected event can include a fall and/or other event. Upon detection of an event, the warning module 118 can cause an alert to be generated to notify the subject and/or other entities about the event. In some embodiments, the alert can comprise a visual and/or auditory alert. In other embodiments, the warning module 118 can be coupled to a communication device 127 (e.g., smart speaker) (FIG. 22) that can notify emergency entity and/or other entity. For example, the warning module 118 can be in communication with a communication device 127 that is capable of making an emergency call and/or otherwise notifying emergency personal and/or other persons.

The smart monitoring system 100 can be applied in a variety of applications. For example, the smart monitoring system 100 can be employed in assistance living areas, where the occupants' movements can be monitored without the compromise of their privacies. The elderly represents twelve percent of the population, and "falls" account for seventy percent of accidental deaths in persons aged seventy-five or older. This technology can be used to alert the caretakers when there is a "fall" and it could also be used to preempt "falls" by predicting when the next "fall" would occur based on the extracted footstep and gait pattern characteristics data. Furthermore, an individual's physical and psychological assessments are possible.

This technology can further be implemented in other applications, including traffic pattern monitoring in an enclosed large setting such as a supermarket, a shopping mall or an airport, where movements of pedestrians could be tracked autonomously, group behaviors could be assessed, and energy and space of the monitored area could be managed. It could also be integrated into a security system.

The monitoring system 100 of the present disclosure is leveraged by cyber-physical system (CPS) techniques. Instead of using traditional privacy violation surveillance technologies, the monitoring system 100 of the present disclosure is designed to sense the footstep induced vibrations to feature the same functions. Based on distributed sensing and processing units, an ubiquitous computing approach to pre-process the data, recognize footstep signals and extract vibration features locally is adopted. Through communications among the sensor network, the system 100 is capable to estimate the occupancy via counting the number of occupants.

In addition, based on the monitoring system 100, a novel indoor footstep localization method that relies on both angle and phase information of the recorded waveforms is proposed. According to the separated pedestrian locations, the different trajectories of multiple people can be tracked. The monitoring system 100 of the present disclosure can be used to analyze footstep signatures, from which the person's physical condition can be inferred, as well as social interactions, from which a psychological assessment can also be possible. In experiments, although the current samples are limited, the proposed system 100 obtains promising results in occupancy Human footsteps induce the floor vibrations, which can be detected to characterize physical conditions of the pedestrian as well as analyze the indoor trajectory pattern to further infer the psychological status. Smart environment technologies help evaluate the physical and emotional health through one's physical movement signature and the social interactions. The cyber-physical system (CPS) with pervasive and ubiquitous computing capability can be leveraged to transform a regular indoor space into a multisensory, autonomous "smart" environment.

As discussed with respect to FIG. 1, the monitoring system 100 can comprise distributed sensor units 103 to detect footstep vibrations, and processing circuitry configured to extract the features corresponding to unique walking and gait patterns. Keeping generality and avoiding violating privacy, the present disclosure does not ask for the identity registration and the number of pedestrians is adequate for the purpose of occupancy estimation. This is similar to the speaker count problem, which requires to estimate the number of speakers participating in a conversation. With no prior information about the speakers, machine learning and deep learning techniques can help solving the problem. Considering the CPS processing power, a light weight system is always preferred.

Related indoor sensing studies typically use vision, RF, mobile, and acoustic methods. And the common location methods include angle-of-arrival (AOA), time-of-arrival (TOA), time-difference-of-arrival (TDOA), Doppler shift frequency-difference-of-arrival (FDOA), or received signal strength (RSS). However, specific sensing conditions and location rules are usually required according to the methodology assumptions, including line-of-sight, high sensor density, carrying wearable devices, and so on. In contrary, vibration-based methods provide easy-to-install sparse sensing, which can be embedded to an Internet of Things (IoT) smart building system.

Characterizing the wave equation, a physical insight on the relationship between the recorded signal and a footstep can be utilized. In addition, since not all traditional techniques are suitable for vibration data from sensors 106, and the specific sensing system has its own properties, a new location method is developed using the sensor-based monitoring system 100 of the present disclosure. This method can consider the acoustic wave properties and given instruments. Based on the location information from different people, the trajectory can be estimated, which can be used to interpret one's behavior patterns, and determine when multiple people are interacting. The social interaction and personal activity pattern analysis can be helpful to physical as well as psychological assessment.

Figure 2:
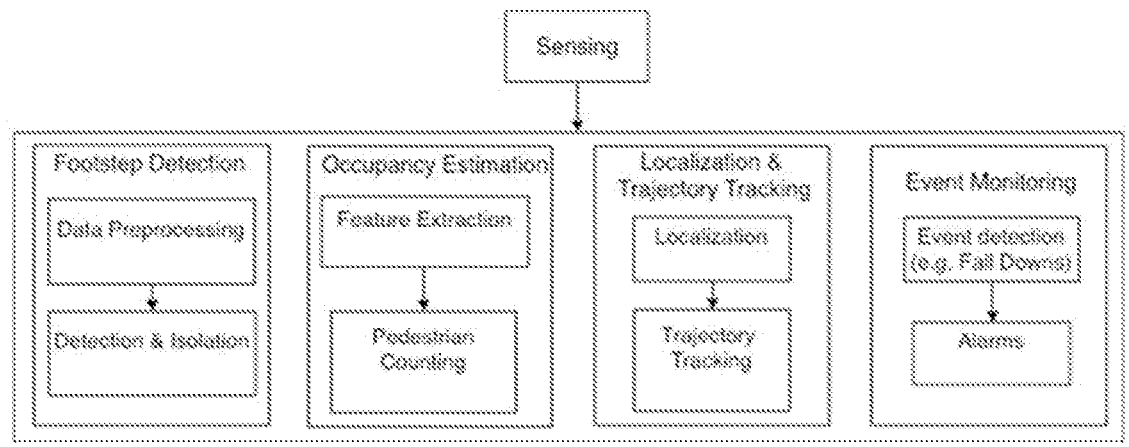
FIG. 2 illustrates an example of a seismic monitoring system workflow according to various embodiments of the present disclosure.

The present disclosure relates to a footstep induced vibration based indoor smart monitoring system 100, which embeds occupancy estimation, localization and trajectory tracking among multiple vibration sensor units 103 comprising sensors 106 (e.g., seismometers). FIG. 2 illustrates an example flowchart associated with the operation of the monitoring system 100 of the present disclosure according to various embodiments. According to various embodiments, an innovative location technique is disclosed that is based on the specific information extracted from the sensor units 106 and the seismic vibration signal model. In various embodiments, an unsupervised machine learning method can estimate the number of pedestrian without any prior information, in addition the footstep signatures have a potential to infer the person's physical condition. According to various embodiments, the footstep trajectory for multiple people can be used for social interaction analysis. According to various embodiments, the sensing unit 103, which embeds a sensor 103 and a computing device 112, in the system carries out sensing, pre-processing, footstep isolation, and feature extraction in a distributed style, while the localization, occupancy estimation and trajectory tracking require communications among sensors. The system 100 of the present disclosure achieves the goals based on both pervasive and ubiquitous computing.

System and Algorithm Design

Sensing

Figure 3:
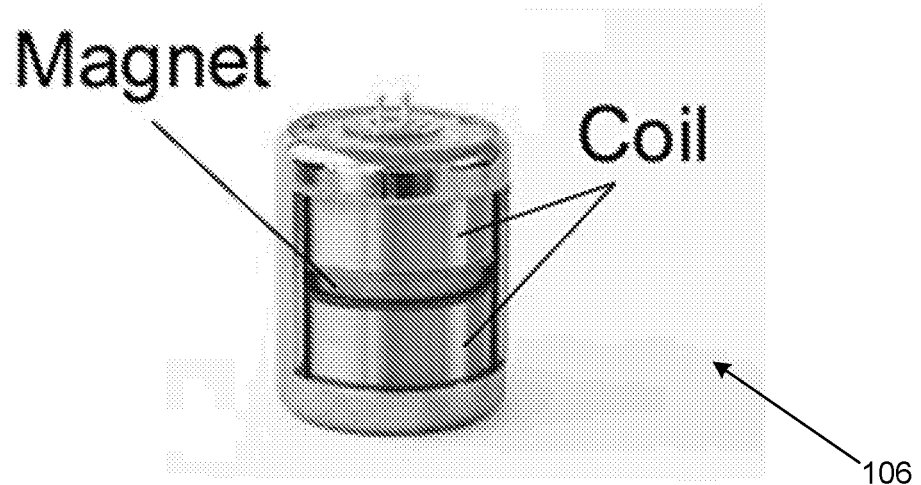
FIG. 3 illustrates an example of a seismometer sensor of a seismic monitoring system according to various embodiments of the present disclosure.

From the mechanics viewpoint, footstep energy travels through the floor media to the vibration sensors. Using networked sensor units 103 attached on the floor, footstep vibration signals are recorded. Different from image and sound sensors, the sensor units 106 of the present disclosure measure the biomedical signatures without entailing personal privacy problem. The sensor unit 103 can comprise a sensitive sensor 106, shown in FIG. 3, to collect vibration data. In some examples, the sensor unit 103 can comprise a sensor 106 with a several hundred Hz sampling rate. Unlike the known methods that use single component seismometers, not only the vertical vibration but also the horizontal vibrations are obtained by the sensors 106. The recorded data respect to the movements on directions North (N), East (E) and Vertical (Z). The data provides for an innovative indoor location approach.

The wanted floor vibration signal in indoor environments is usually weak, especially when the footsteps are far away from a seismometer, resulting in a low signal to noise ratio (SNR). Amplifiers 109 can be used to amplify weak vibration signals to facilitate detection as well as the following processing tasks. There is a built-in analog-to-digital converter (ADC) in the sensor unit 103 recording board to convert the analog signals to digital signals. A low-cost computing device 112, such as a Raspberry Pi, for example, can be employed to record data, apply computation tasks locally and communicate with other units.

The computing device 112 of the present disclosure can receive the data from the sensor 106 and saves the raw data to a local database. In order to process data in real time and obtain accurate location results, the sensor synchronization is important. The computing device 112 is the core of the CPS system because it is in charge of collecting and storing data, processing data analytics, communicating with other units and providing raw and processed data to the visualization tool.

Footstep Detection

To extract footstep signals from the background for analysis, the noises from the recorded data need to be removed. Then a footstep isolation step is implemented to isolate the footstep vibrations.

Preprocessing

The building is constantly shaking and generates the background vibration noises to the interested footsteps vibration. Besides, the air conditioners (AC) and other appliances also generate all kinds of vibrations. Unlike simple environment noise, which can be removed using a high pass filter, background noise associated with the present disclosure is not limited at a given frequency range. Therefore, in order to improve the SNR, the background noise needs to be removed adaptively. A wavelet denoising technique can be applied on the recorded data to suppress non-stationary noises. However, instead of using a fixed threshold, a relative threshold according to the signal strength can be used.

The denoised signal $s_d$ using wavelet thresholding can be expressed as:

$$s_d = \sum_{j,k \in K} r\left(\int s(x) \psi_{j,k}(x) dx\right) \psi_{j,k}, \quad (1)$$

Where $(\psi_{j,k})_{jk \in K}$ denotes the orthogonal wavelet basis, $\tau(\cdot)$ is the thresholding operator adapt to the signal energy.

Footstep Detection and Isolation.

After denoising, a signal segmentation step is applied to extract the footstep vibrations, which means a footstep-induced signal needs to be recognized apart from the background noises. Considering the complexity and efficiency, a change point detection algorithm is adopted, e.g., STA/LTA method, which is usually applied in the seismic event detection. The STA (short time average) is sensitive to rapid fluctuations in the amplitude of the time series, whereas the LTA (long time average) provides information about the background noise. In order to generalize the footstep isolation method, the STA/LTA method can be rewritten as STCF/LTCF, where CF stands for characterization function which characterizes waveform properties:

$$\frac{STCF_i}{LTCF_i} = \frac{\frac{nl}{ns} \sum_{j=i-ns}^{i} CF_j}{\sum_{j=i-nl}^{i} CF_j}, \quad (2)$$

where, i,j are the sample number, ns and nl represent the short and long window lengths. Note that CF can be any kind of signal statistics depending on the applications. The footstep onset is picked when the STCF/LTCF ratio reaches the defined threshold, then the ratio will drop to cross the threshold again when the ending is picked.

Occupancy Estimation

The occupancy estimation means to count the number of occupants over a given time period. In order to implement this function, an unsupervised machine learning method is used. First, the monitoring system 100 extracts features of footstep events. Then a clustering type machine learning model is generated to estimate the occupancy. The traditional person identification projects used supervised machine learning models, such as support vector machine (SVM) and its derivations. Since the occupants are not registered, the monitoring system 100 of the present disclosure uses clustering to estimate the number of walking people rather than who is walking. In addition, instead of using a supervised model, such as k-nearest neighbor classier, the present disclosure uses an unsupervised model to enhance the versatility of the system, as no pre-registration or prior models are needed.

---
Algorithm 1: Footstep detection algorithm

1: Input: Raw vibration data acquired from seismometers
2: Output: Segmented footstep vibration signals;
3: Initialization
    Seismometer synchronization;
    Data conditioning to maintain the same sampling rate and regularized time stamps;
4: Denoising dependent on signal stregnth
5: Footstep detection based on signal time series statistics;
6: Extracting footstep vibration signal segments based on the detected onset and ending positions.

---

Feature Extraction.

To characterize the footstep signatures, features should be extracted. The vibrations and sound pressure responses of human footsteps in buildings can be broadband and frequency-dependent. Different vibration signatures from different walking styles have been studied. The footstep features include the single footstep features, as well as gait features. According to various embodiments of the present disclosure, features in both time and frequency domains are computed, including standard deviation, peak values, entropy, partial signal before and after the maximum peak, spectrum centroid, locations and amplitudes of peaks, power spectrum density, etc. In addition, in some embodiments, based the extracted features, the human physical conditions can be analyzed based on the extracted features.

Pedestrian Counting.

According to various embodiments, a clustering technique estimates the number of the occupants. Clustering techniques group similar objects, which are the extracted footstep features. The classic "k-means" method minimizes the mean squared distance from all points to their respective cluster centers, but the "k" needs to be defined beforehand. In some known methods, a Markovian framework has been used for occupancy estimation. However, it is too computational expensive for a real time, on-line processing in Internet of Things (IoT) devices. In addition, to broaden the application range, no prior information should be assumed.

According to various embodiments, the density-based spatial clustering of applications with noise (DBSCAN) technique is used, which is a density-based clustering algorithm to group close sample points in the latent space. DBSCAN starts with a random starting point that has not been clustered. If it contains sufficiently neighboring points, a cluster is formed. Otherwise, the point is labeled as noise. The algorithm can be found in Algorithm 2.

---
Algorithm 2: Occupancy estimation algorithm

1: Input: Footstep vibration segments
2: Output: Pedestrian number according to the number of clusters.
3: Feature extraction
    Time domain feature extraction;
    Frequency domain feature extraction;
    Feature space configuration
4: Pedestrian counting
    Feature space dimension reduction;
    Find the $\epsilon$ neighbors of every point in the latent space;
    Identify the core points with at least minimum number of neighbors;
    Find the connected components of core points on the neighbor graph;
    Assign each non-core point to a nearby cluster if the cluster is an $\epsilon$ neighbor;
    Assign the point it to noise, if the cluster is not an $\epsilon$ neighbor;
    Until convergence, count the number of clusters.
5: Footstep detection based on signal time series statistics;
6: Extracting footstep vibration signal segments base on the detected onset and ending positions.

---

Localization

Figure 5:
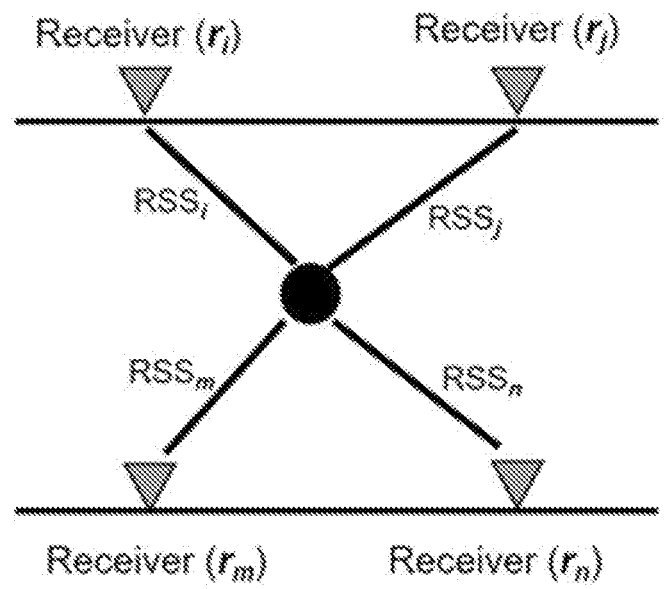
FIG. 5 illustrates an example of a seismometer sensor layout for the seismic monitoring system according to various embodiments of the present disclosure.

The typical location methods such as AOA, TOA, TDOA, FDOA, and RSS, were mostly designed for RF or Wi-Fi signals with sensor arrays. In addition, different than radio wave propagation, which can be disturbed by the obstructions in the space, footstep vibration signals propagate through the floor. So the traditional RF and reflection based location methods are not suitable for the monitoring system of present disclosure. Since the system of the present disclosure uses the isolated seismometers instead of sensor array systems, the typical beamforming techniques cannot be adopted. FIG. 5 shows a sketch of the sensor-based location system 100. There are N sensors 106 at known (x,y) coordinates, $r_n = [x_n, y_n]^T$, n=1, ..., N and $S = [s_1, s_2, ..., s_N]$ are detected footsteps.

Initialization.

Location techniques require the prior knowledge of the propagation velocity and the sensor locations. The GPS accuracy is lower inside a building and not to mention the sensors 106 are placed too close. To begin, the relative sensor locations are manually placed to build a system map. Then, in the defined coordinates, a hammer test is applied to validate the sensor synchronization and initialize the wave propagation velocity model of the floor.

Angle of Arrival (AoA).

Figure 6:
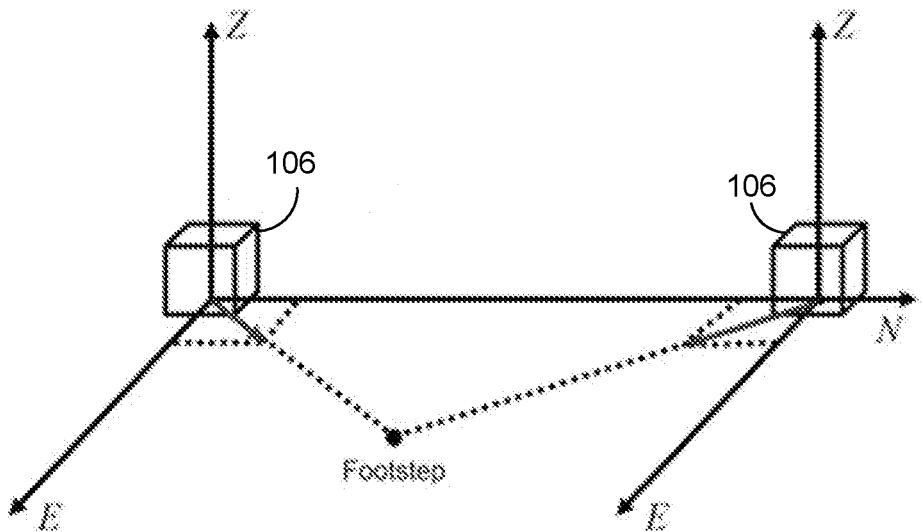
FIG. 6 illustrates an example of angulation technique used by a seismic monitoring system according to various embodiments of the present disclosure.

Typically, AoA based approaches use antenna arrays to estimate the incident angle of the transmitted signal. However, without antenna arrays, the system of the present disclosure uses a modified AoA method. FIG. 6 shows a sketch of how angulation technique can work in the system setup. The object's position is determined through the intersection of a number of pairs of angle directions. The main advantage of AoA is that the device/user location can be estimated with as low as two monitors in a two dimensional (2D) environment, or three monitors in a three-dimensional (3D) environment respectively. In addition, AoA can provide accurate estimation even when the transmitter-receiver distance is small, which makes it an appropriate option for the indoor localization.

For estimating the location of any entity in 2-D, the method requires at least two known reference points (seismometer locations) and two angles ($\theta_1, \theta_2$), respectively. To obtain the wave propagation angles, the sensor 106 can be useful. The received data includes two orthogonal ground-motion records corresponding to the east and north components (respectively noted E and N). Configuration of a 2×2 covariance matrix over the two components is:

$$C = \begin{pmatrix} Cov(E, E) & Cov(E, N) \\ Cov(N, E) & Cov(N, N) \end{pmatrix}, \quad (3)$$

where Cov(·) denotes the covariance.

The eigenvectors of the Equation (3) form an orthogonal base, from which the wave orientation can be estimated. The eigenvalues are organized so that $\lambda_1 \geq \lambda_2$ with $U_i$, i=1, 2 as the eigenvector. Then, the wanted angle $\theta$ is the direction of $U_1$.

Phase of Arrival (PoA).

Figure 7:
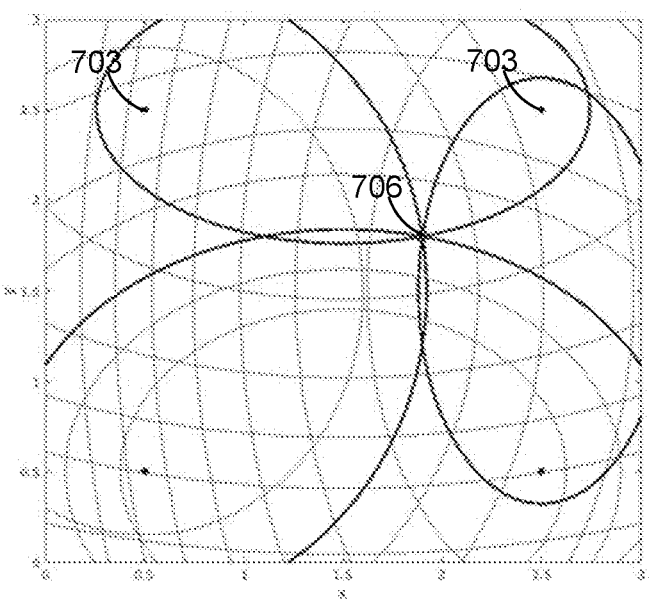
FIG. 7 illustrates an example of location by means of Phase of Arrival (PoA) evaluation according to various embodiments of the present disclosure.

PoA based approaches use the phase or phase difference of carrier signal to estimate the distance between the transmitter and the receiver. However, PoA based approach requires line-of-sight for high accuracy, which is rarely the case in indoor environments. FIG. 7 shows the POA principle. In FIG. 7, the lines show the equal phase, the black dots 703 are the receivers, and the red dot 706 is the estimated location. The phase difference between every two sensors 106 can be used to plot a series of equal phase curves, which typically are ellipses. Then, all the equal phase curves should intersect at the true location point. Theoretically, three sensor pairs can locate one point in a 2-D plane. And with more observations (sensor pairs), the location will be more accurate.

It is natural that if the distances between footstep location and sensor are the same or integral times of the wavelength, the phase difference would be zero. Otherwise, the phase difference between two received signals can be directly used to estimate the distance:

$$d = \frac{\lambda}{2}\left(\frac{\varphi}{2\pi} + n\right), \quad (4)$$

where $\lambda$ is the wavelength, $\varphi_d$ is the phase difference, and n is an integer. The wave propagation speed is c and the $\lambda = c/\omega$. The phase difference of the received signals can be calculated directly from the signals, but the range of the phase measurement is between 0 and $2\pi$, it would be necessary to recognize the passed number of whole cycles n in order to determine the one-way distance greater than $\lambda/2$.

Phase Constrained Angle of Arrival (PAoA).

Figure 8:
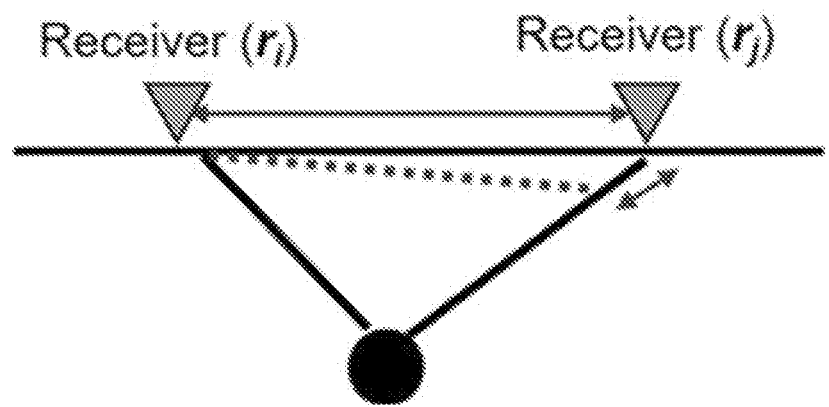
FIG. 8 illustrates an example of a proposed Phase constrained Angle of Arrival (PAoA) technique for location estimation according to various embodiments of the present disclosure.

According to various embodiments, a novel location method called phase constrained angle of arrival (PAoA) is proposed that combines the AoA and PoA methods. AoA principle was shown in FIG. 6, where location is determined by the intersection among the arrival directions estimated from different sensors 106. So the inaccurate angle estimation, which can be brought from interferences in the isolation and the waveform distortions, will result in location uncertainties, shown in FIG. 8.

From Equation (4), assume d is the distance between the sensor 106 and the footstep location, then the recorded phase $\varphi$ on certain $\omega$, is:

$$\varphi = 2\pi\left(\frac{2d\omega}{c} - n\right). \quad (5)$$

Thus, if the n is known, either Equation (4) or Equation (5) can be used to infer the distance. Based on this phased related distance information, the location obtained from AoA will be constrained to a smaller area, which may not be the ground truth location as PoA results could also have uncertainties.

To sum up a general formula, consider the localization system receives a set of signals from N seismometers placed at known locations $r_i$, (i=1,2, . . . , N) and obtains a set of measurements $x_1, x_2, \ldots, x_n$. There is a linear relationship between these two variables as:

$$x_i = g(r_i) + e, \quad (6)$$

$$x_i = g(r_i) + e. \quad (6)$$

where g(·) is the function of the position of the seismometer $r_i$ and e is the error in location estimation with a probability distribution function $p_e(e)$. The maximum likelihood estimate of the position is the point that maximizes the probability of the location results over all sensors at the same time:

$$\hat{x} = \arg\max p(x \mid r). \quad (7)$$

Trajectory Tracking

Once the footstep locations are determined, the trajectory of a pedestrian can be estimated. The footsteps from different people can be separated, and the footsteps are not fully overlapped, the trajectory map of one area can be obtained by stacking all trajectories from different people. In order to overcome the interferences of noise and uncertainty in the location results, an extended Kalman filter (EKF) is used to infer the true underlying nonlinear pedestrian trajectories.

Assume the monitoring system 100 of the present disclosure receives a sequence of detected footsteps, $s_1, s_2, \ldots, s_k$, located at position $z_k$ with a time stamp, $t_k$. Then, $x_k = f(x_{k-1}, u_k) + w_k$ and $z_k = h(x_k) + v_k$ can be used to denote the transition and observation equations, respectively, where $u_k$ is the control vector, $w_k$ and $v_k$ are the process and observation noises which are both assumed to be zero mean, and $Q_k$ and $R_k$ are the covariance of multivariate Gaussian noises. The function $f$ computes the predicted state from the previous estimate. The function h computes the predicted measurement from the predicted state. At each step, the Jacobian (partial derivative matrix) is evaluated with current states for update.

---

Algorithm 3: Location and trajectory tracking algorithm.

---

1: Input: Footstep vibration signals from a single pedestrian.
2: Output: Trajectory tracking results
3: Location
   Using AoA method to locate the footsteps based on the vibration signals obtained from E and N components from at least two sensors;
   Using PoA information to improve the location accuracy;
4: Trajectory tracking
   Predict
      predict state estimate $\tilde{x}_{k|k-1} = f(\hat{x}_{k-1|k-1}, x_k)$
      predict covariance estimate $P_{k|k-1} = F_k P_{k-1|k-1} F_k^T + Q_k$
   Update
      update residual $\tilde{y}_k = z_k - h(\hat{x}_{k|k-1})$, covariance $S_k = H_k P_{k|k-1} H_k^T + R_k$,
      near-optimal Kalman gain $K_k = P_{k|k-1} H_k^T S_k^{-1}$, state estimate $\tilde{x}_{k|k} = \tilde{x}_{k|k-1} + K_k \tilde{y}_k$
      and covariance estimate $P_{k|k} = (I - K_k H_k) P_{k|k-1}$
      where the state transition and observation matrices are defined following Jacobian format:

$$F_k = \frac{\partial f}{\partial x}\bigg|_{\hat{x}_{k-1|k-1}, u_k} \text{ and } H_k = \frac{\partial h}{\partial x}\bigg|_{\hat{x}_{k|k-1}}$$

---

Experiment and Evaluation

Experiment Setup

To evaluate the monitoring system, experiments were conducted with footstep induced vibration signals collected when pedestrians were asked to walk in an office area with designated number of occupants.

Figure 4:
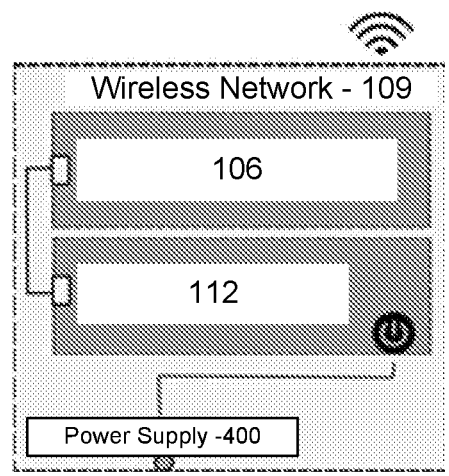
FIG. 4 illustrates a hardware schematic of a seismic monitoring system according to various embodiments of the present disclosure.

As discussed in FIGS. 1 and 4, the system hardware configuration of the monitoring system 100 can comprise a computing device 112 (e.g., a Raspberry Pi board), a power supply 400 and a sensor 106. In various embodiments, hardware components are housed in a waterproof box called R1 to protect them from harsh environment. A power supply 400 can comprise a battery, and/or any other type of power supply as can be appreciated. For example, the battery can comprise a 11V battery and 99.9 Wh can be further integrated. The sensor units 103 can be installed on the floor and the sensors 106 in the systems form a sparse mesh network.

Figure 9:
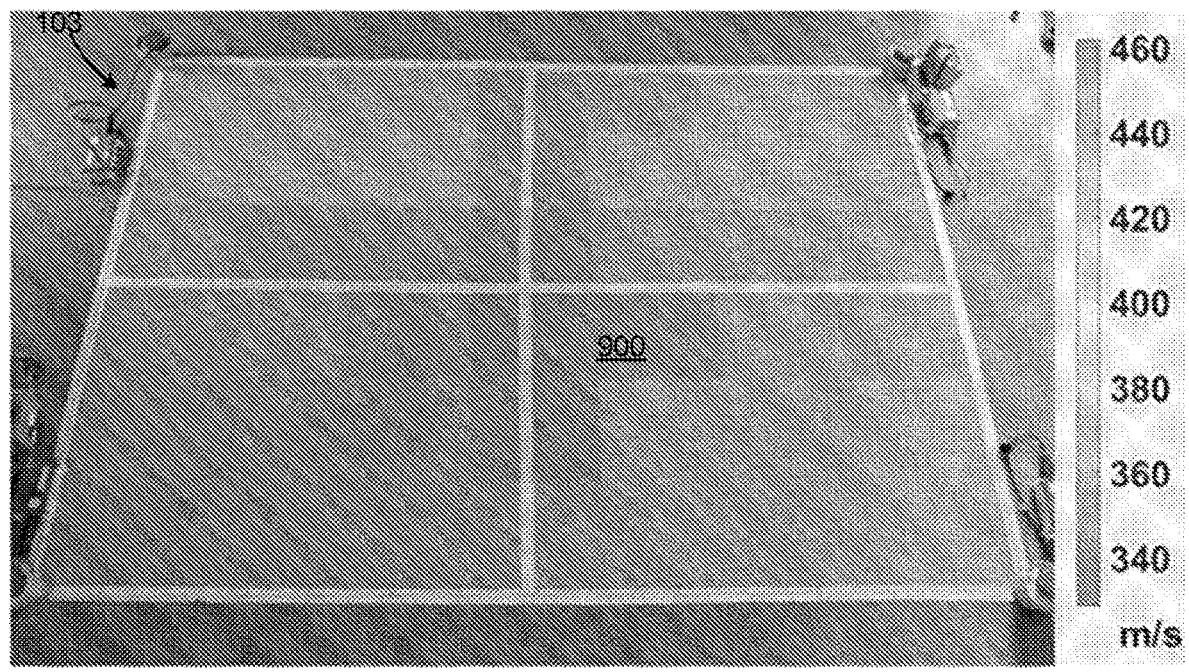
FIG. 9 illustrates an example of initializing a floor velocity model according to various embodiments of the present disclosure.

In the experiment, there are four pedestrians walking in a fixed area 900 as shown in FIG. 9. Notice that the sensor units 103 can be placed at the corners of the testing area 900. In the setup, two sensor units 103 are arranged with a distance at 3 m and 4 m, so when a person walks by the sensors 106, the sensing units 103 are far enough that the footsteps do not fully overlap. The sampling rate is set to 500 Hz. The features are extracted, and values are normalized for clustering.

Figure 10:
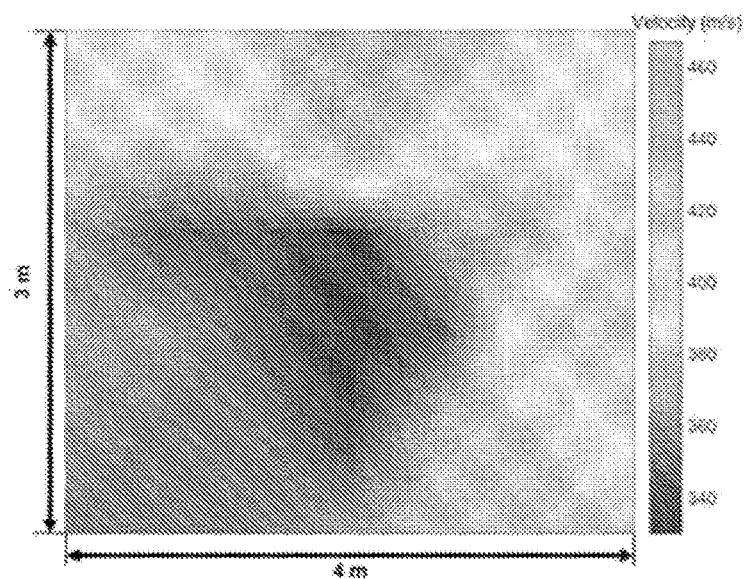
FIG. 10 illustrates an example of a plot of an interpolated velocity model according to various embodiments of the present disclosure.

To initialize the floor velocity map, a hammer test is carried out to generate impulse signals. As the ground truth of the hammer location is known, based on the time differences among sensors 106, the floor velocity can be estimated. From FIGS. 9 and 10, the average floor velocity is about 400 meters per second (m/s). From the spectra in FIG. 12, the analysis frequency can be 200-300 Hz. So the wavelength is between 1.3 meters (m) and 2 m. Thus, the integral n for PAoA is easy to determine.

After the system initialization, there are two main parts: occupancy estimation and trajectory tracking. In the former part, the unsupervised clustering is used to identify the number of people, and provide the accuracy. In the latter part, people are asked to walk randomly in the area and try to track their trajectories, even when the location results could be contaminated with noises or not accurate.

Evaluation

Footstep Detection.

Figure 11:
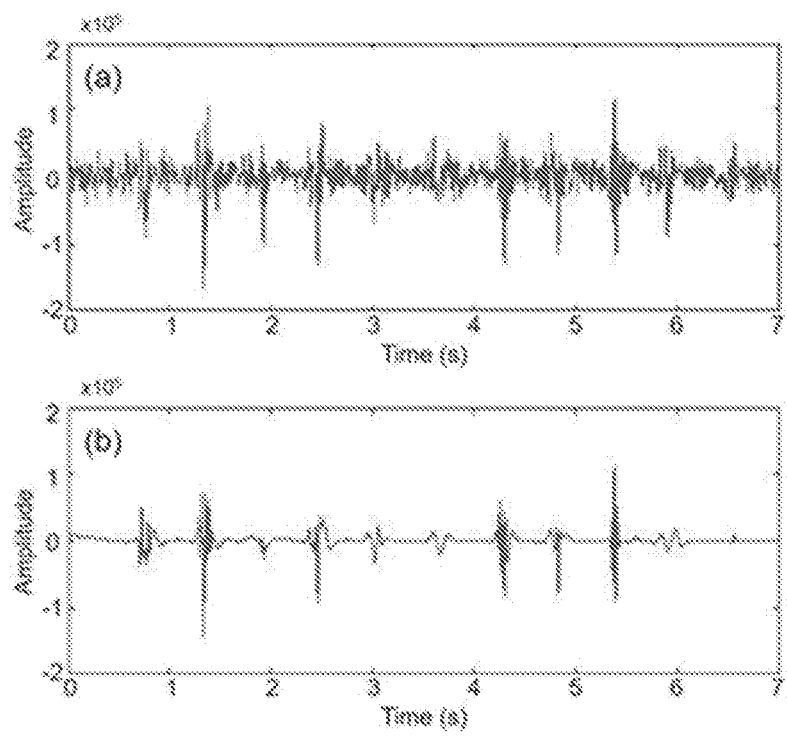
FIG. 11 illustrates an example of plots of raw data before denoising and after denoising according to various embodiments of the present disclosure.
Figure 12:
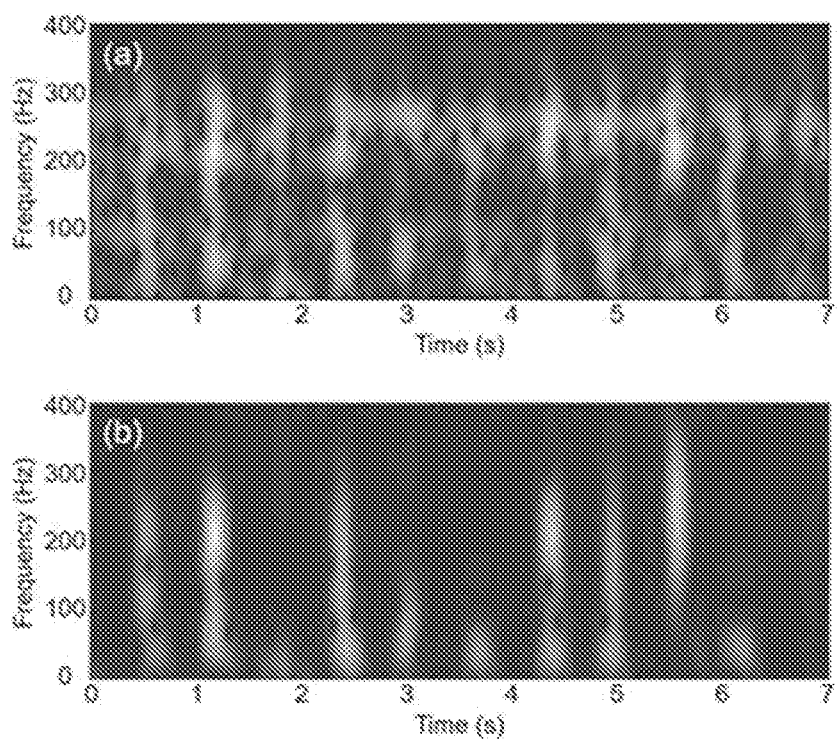
FIG. 12 illustrates an example of a spectra before and after denoising according to various embodiments of the present disclosure.

The first step of footstep detection is pre-processing. FIG. 11a shows a raw data example. It is clear that the background noise is not limited at a given frequency range, so a simple bandpass or high pass filter cannot generate satisfied filtering results. The time domain denoising result based on the wavelet thresholding method is shown in FIG. 11b. FIG. 12 displays the spectra of the signals before and after filtering, where spectral distributions of the footstep-induced vibrations and noises can be observed. The noise is broadband and frequency-dependent. It is clear that the noise has been removed both in the time and frequency domains.

Figure 13:
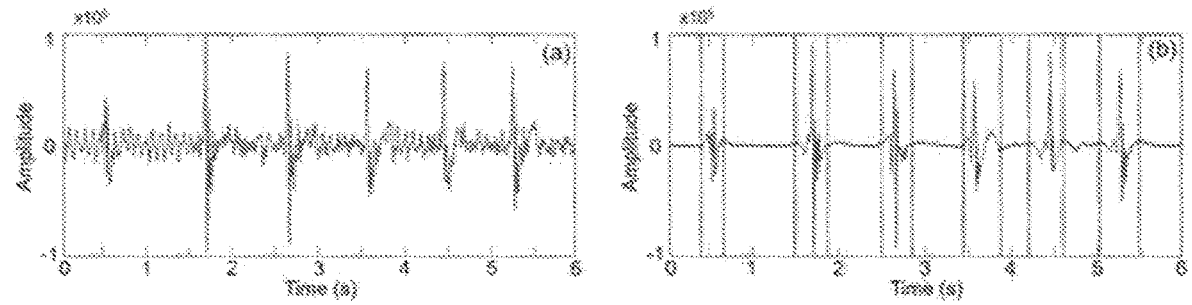
FIG. 13 illustrates an example of plots of footstep isolation data showing raw data and isolated footstep vibrations from denoised data according to various embodiments of the present disclosure.

The next step is the footstep isolation. In this application, the second order statistics are used to highlight amplitude changes. FIG. 13 shows footstep isolation results, where the signals between blue (onset) and pink (ending) bars are recognized footstep vibrations.

Occupancy Estimation.

In the experiment, only the number of occupants from one to four is investigated, which is sufficient based on the research in group walking behavior that shows that multiple people tend to walk in smaller units. First, a feature space which has more than forty dimensions is generated, but some features are redundant. Thus, a feature selection step is applied to remove features with little contributions or even counter effects. The left features are vibration duration, standard deviation, entropy, maximum peak location, peaks before maximum value, centroid frequency, and centroid frequency location. Through the feature selection, the accuracy has been improved.

The following table shows the clustering accuracy in the experiment.

TABLE 1

Occupancy estimation accuracy (maximum 4 people walking).

|  | 1P | 2P | 3P | 4P |
|---|---|---|---|---|
| Accuracy | 92.06% | 88.89% | 89.79% | 87.83% |

In the experiment, people are grouped from one (1) to four (4_, and footsteps are recorded. Then, the unsupervised clustering method is used to estimate the cluster number. It is not surprised that the highest accuracy is achieved for the single person walking scenario. However, the three people identification accuracy is higher than the two people identification. The reasons could be related to the data set, because there is limited data, the hyper parameter selection is influenced by the existing people. Though four people identification accuracy is lower than other cases, 87.83% is still a better result compared with the prior methods.

Location.

Figure 14:
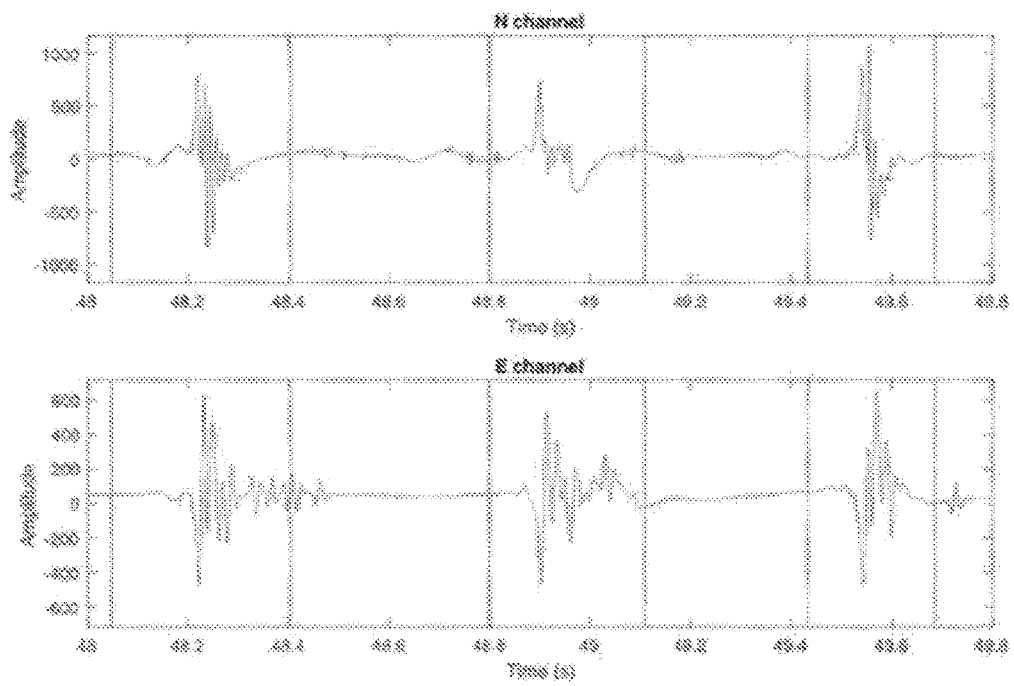
FIG. 14 illustrates an example of plots showing footstep vibrations recorded by the same seismometer but on two different channels according to various embodiments of the present disclosure.

According to various embodiments, the PAoA method of the present disclosure combines the AoA and PoA methods together for better location accuracy. The first step of PAoA is to estimate the footstep signal arrival angles based on the amplitudes from different axes of the sensors 106. The received data is assumed to have two orthogonal ground-motion records corresponding to the east and north components (respectively noted E and N). The two channel amplitudes are the projection results of the true amplitude. The different waveforms because of the projection effect from N and E channels of the same footsteps are shown in FIG. 14. Using Equation (3) and the corresponding eigenvector estimation approach, the projection angle of one footstep vibration can be estimated.

Figure 15:
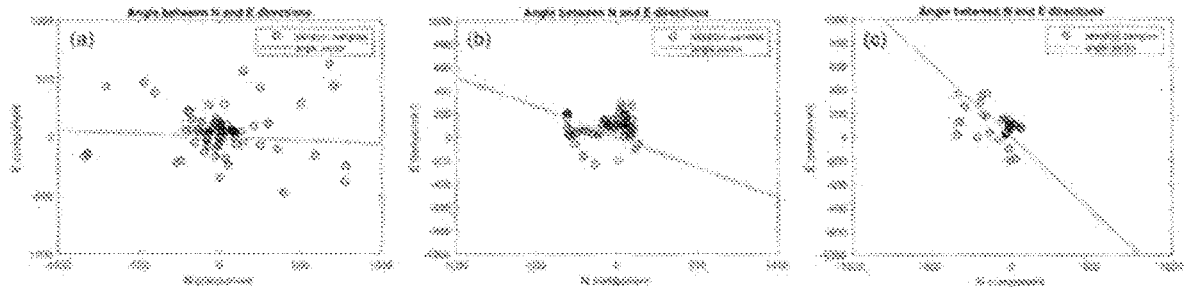
FIG. 15 illustrates example plots showing angle vectors corresponding to the footsteps of FIG. 14 according to various embodiments of the present disclosure.

There are three segmented footsteps in FIG. 14. Since people were asked to walk past the sensor 106, the arrival angles of these footsteps should be different. FIG. 15 shows the footstep angles to the sensor 106 is changing gradually as the footstep locations are different when people are walking, resulting in different relative angles. After AOA, based on the PoA principle, the phase information is estimated to improve the location accuracy.

Figure 16:
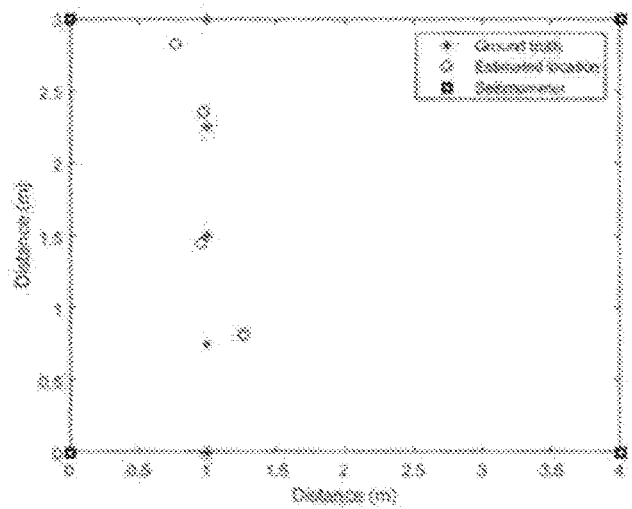
FIG. 16 illustrates an example plot of footstep location according to various embodiments of the present disclosure.

FIG. 16 shows a footstep location example using the proposed PAoA. In the preliminary results, the location accuracy is around 30 cm, which has not been testified in theory. Notice that the bottom footstep is not located in the figure, as the location result is out of the testing area. Though it is common to have boundary issues, further work will be done to fix this kind problems.

Trajectory Tracking Results.

Figure 17:
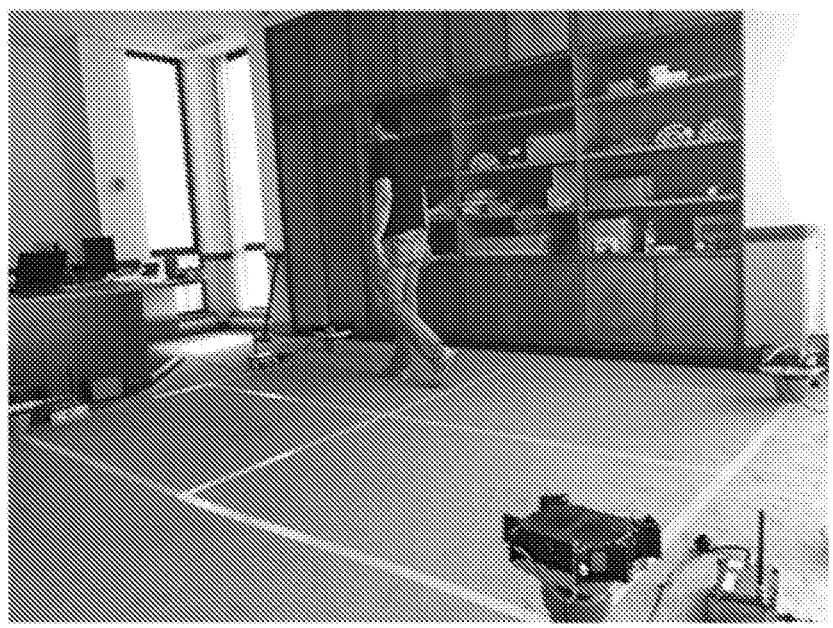
FIG. 17 illustrates an example of a trajectory tracking experiment using a seismic monitoring system where a single person walks randomly according to various embodiments of the present disclosure.
Figure 18:
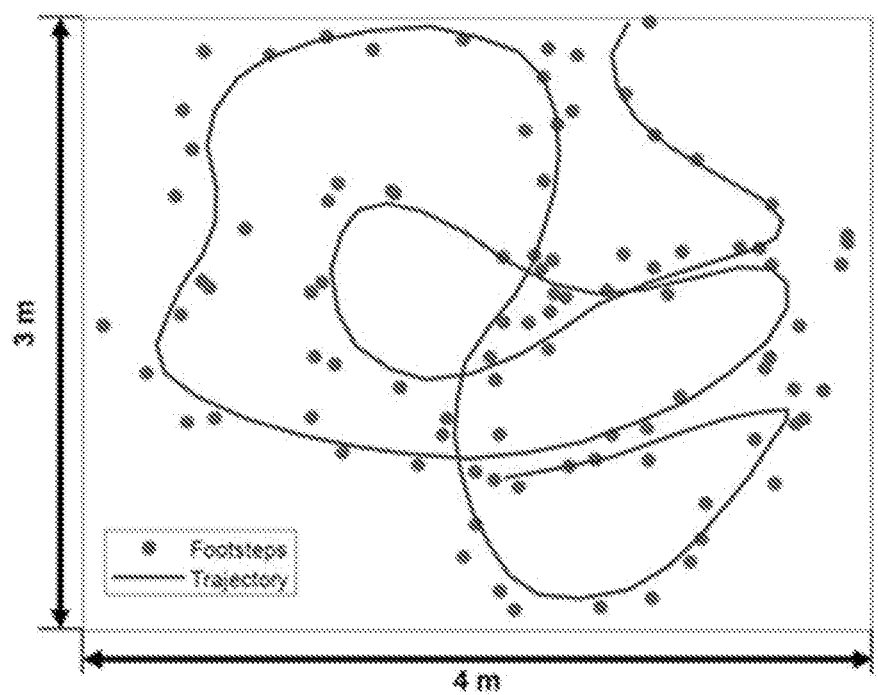
FIG. 18 illustrates an example plot of the results of the trajectory tracking experiment of FIG. 17 for a single person walking randomly according to various embodiments of the present disclosure.
Figure 19:
FIG. 19 illustrates an example of a trajectory tracking experiment with two people walking randomly according to various embodiments of the present disclosure.
Figure 20:
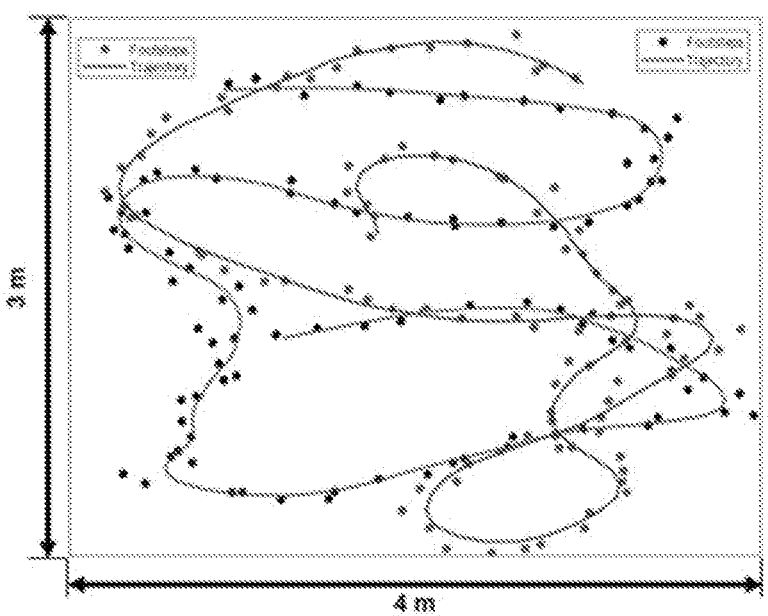
FIG. 20 illustrates an example plot of the results of the trajectory tracking experiment of FIG. 19 according to various embodiments of the present disclosure.

Compared to the size of human body, the obtained footstep location is "accurate", but interferences and uncertainties in the location results make the direct trajectory estimation based on footstep locations rarely possible. The EKF is applied to estimate the true trajectory. The pedestrian walking experiment has some stages, as a different amount of people walking are randomly in the same area. FIGS. 17 and 18 show a single person experiment. One person is walking randomly in the testing area, and his footstep locations are recorded, then the trajectory is estimated. FIGS. 19 and 20 show a two people randomly walking example. Because people are separated first, more than one random walking person does not affect each other. However, with more people, the identification accuracy will be lower which will further reduce the location accuracy, resulting in problematic trajectory tracking results. Based on the results in FIG. 20, the social interactions among multiple people can be inferred.

A Footstep Induced Vibration Signature

Here, the vibration signature expression is derived based on the wave equation. The recorded signal s(t) can be viewed as the summation of the vibration waveform u(t) and noise ε:

$$s(t) = u(t)\varepsilon. \tag{8}$$

The footstep induced vibration u(t) can be modeled as an acoustic signal in the format of a convolution between the footstep force F(·) and the Green's function G(·):

$$u(r, t) = G(r, t)F(t), \tag{9}$$

where, r is the distance, and G(·) describes the site effect between the vibration location and the sensor location. In many applications the Green's function is the solution of a differential equation with a delta function as excitation. The motion of the monitoring system 100 is assumed to be governed by the Helmholtz equation:

$$\nabla^2 u + k^2 u = 0, \tag{10}$$

where the wave number k is related to the angular frequency ω and satisfies k=ω/c. Here, the normal modes of a string model are derived by $$u_m(x) = \frac{1}{\sqrt{R}} \sin k_m r, \tag{11}$$

where, m is the mode number, R is the model size, $$k_n = \frac{m\pi}{2R}$$

is the wave number. Equation (11) is derived based the boundary conditions that the end points of the string are fixed (u(0)=u(2R)=0). In addition, the string vibration frequencies are $$\omega_m = \frac{m\pi c}{2R}. \tag{12}$$

Considering the attenuation effect, derived the eigen frequency ($\omega_m^{(a)}$) with the intrinsic attenuation:

$$\omega_m^{(a)} = (\pm 1 - i\gamma)\omega_m, \tag{13}$$

where γ is the attenuation coefficient. The waveforms in this string model with the intrinsic attenuation are given by the summation of normal modes:

$$u(r, \omega) = \sum_{m=0}^{\infty} \frac{u_m(r) \int u_m * (r')F(r')dr'}{\left(\omega \frac{(a)}{m}\right)^2 - \omega^2}. \quad (14)$$

Equations (8), (11), and (14) together formulate the received signal on the sensor units 103. Here, a harmonic model is used to represent the periodical signals from the event location. The signal $s_{r_i}(t)$ from the receiver $r_i$ can be modeled as a summation of different harmonic waves:

$$s_{r_i}(t) = \sum_{k=1}^{K} A_k \cos(\omega_k t + \varphi_k), \quad (15)$$

where, k=1, . . . ,K denotes the kth harmonic components, $A_k$ represents the amplitude, while $\omega_k$ is the centroid frequency, $\varphi_k$ is the phase.

Observation Model

Once the features are extracted, a clustering strategy is constructed to recognize many people/occupants are recorded. Before the introduction of the clustering technique, another challenge is the possible footstep signal overlap of different occupants. Assume there are k impulses, $s_1, \ldots, s_k$ happening at approximately same time, $a_{i,j}$ is the signal decay coefficient, which is determined by the footstep location relative to different sensors 106, and the observations at the N sensors 106 are O=As, where $$O_1 = a_{1,1}s_1 + a_{1,2}s_2 + \ldots + a_{1,k}s_k, \ O_2 = a_{2,1}s_1 + a_{2,2}s_2 + \ldots + a_{2,k}s_k, \ O_N = a_{N,1}s_1 + a_{N,2}s_2 + \ldots + a_{N,k}s_k. \quad (16)$$

Because of the spatiotemporal variations, the signals are not fully overlapped.

Figure 21:
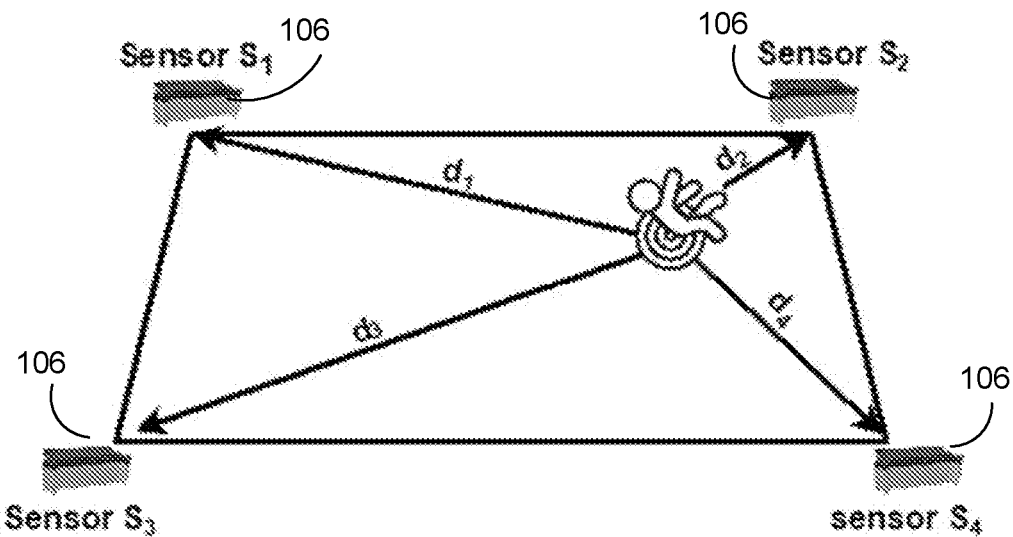
FIG. 21 illustrates an example of event detection and location in a room, in this case a person "fall down", according to various embodiments of the present disclosure.

Turning now to FIG. 21, shown is an example of event location on a room. In this case, the event could be generated by a fall down. The triangulation of information by the sensors allows the location estimation.

Figure 22:
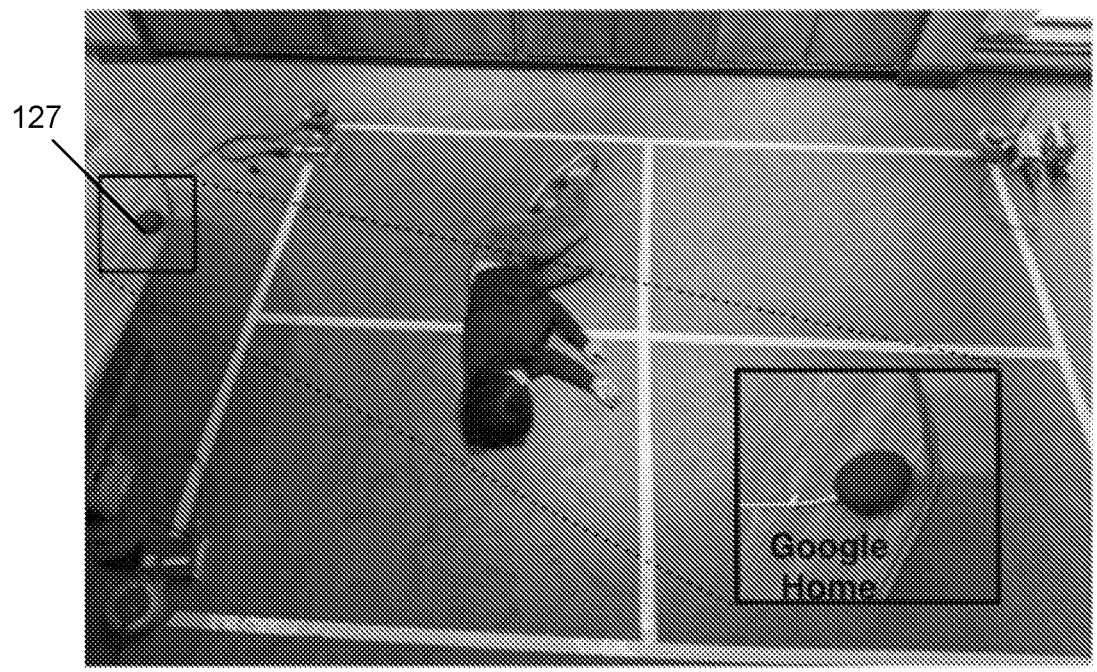
FIG. 22 illustrates an example of person fall down, detection, location, and notification via smart device according to various embodiments of the present disclosure.

FIG. 22 illustrates an example of a detected and located fall down. The system 100 is able to send alerts via additional communication devices 127 (e.g., smart speaker).

Figure 23:
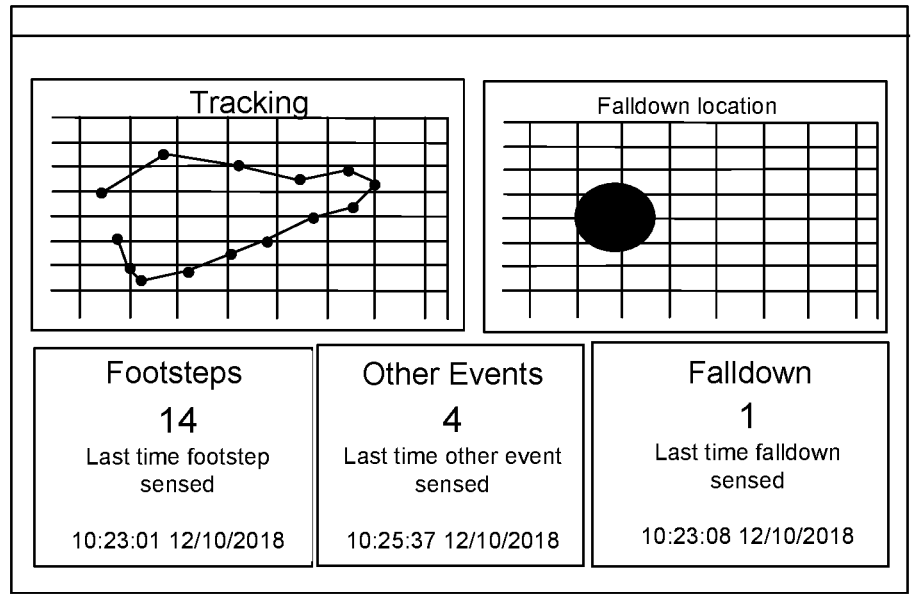
FIG. 23 illustrates an example of a user interface generated by the seismic monitoring system according to various embodiments of the present disclosure.

Turning now to FIG. 23, shown is an example user interface 2300 generated by the seismic monitoring system 100 of the present disclosure. In particular, the user interface 2300 of FIG. 23 includes trajectory tracking, number of detected footsteps, a last time a footstep was sensed, a number of detected other events, a last time another event was sensed, a fall down location, a number of detected falls, a last time a fall down was sensed, and/or other information.

Trajectory tracking: In this element card, the user can see in real time the trajectory of the person sensed by the seismic sensor on the floor.

Number of detected footsteps: The system displays how many footsteps the system has counted in that specific range of time.

Last time sensed—footstep: The time (hour+date) of the last footstep sensed by the system is displayed in this card of the dashboard.

Number of detected "other" events: If the detected event is neither a footstep nor a fall down, this event is classified as "other events". This element card displays the number of this types of events that have been sensed in that period of time.

Last time sensed—other events: The time (hour+date) of the last "other" events sensed by the system is displayed in this card of the dashboard.

Fall Down location: Once the system senses a fall down, the location is displayed in this element card.

Number of detected fall downs: The system displays how many fall downs the system has counted in that specific range of time.

Last time sensed—fall downs: The time (hour+date) of the last fall down sensed by the system is displayed in this card of the dashboard.

Figure 24:
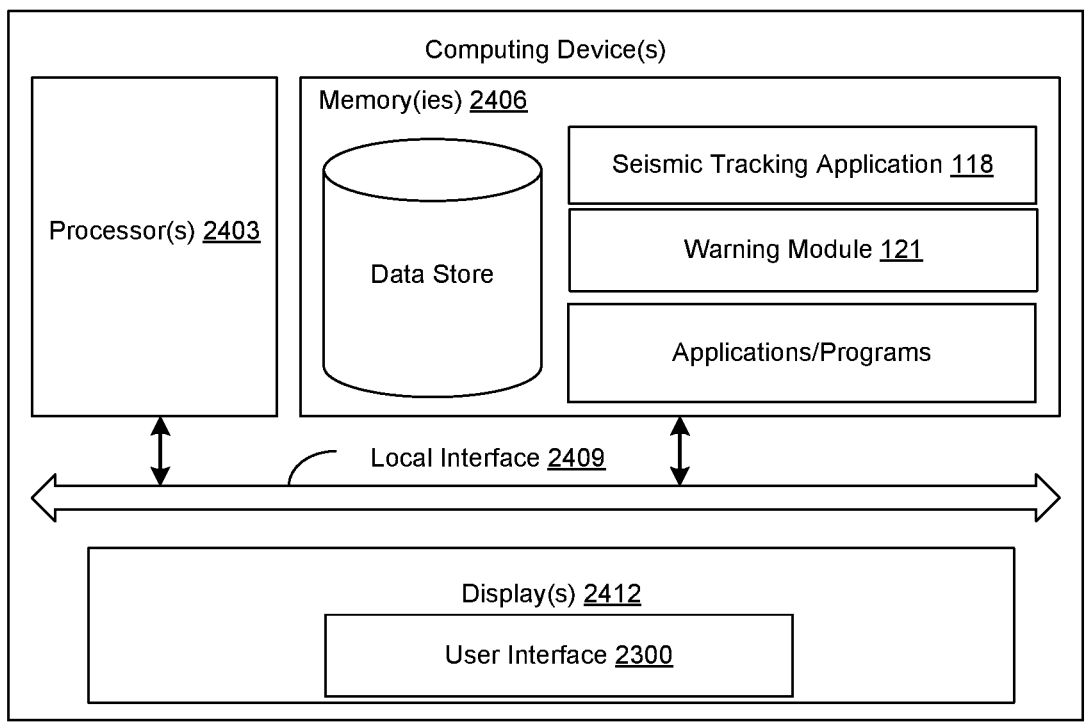
FIG. 24 is a schematic block diagram that provides one example illustration of a computing environment according to various embodiments of the present disclosure.

With reference now to FIG. 24, shown is one example of at least one computing device 106 (e.g., an interfacing device, a server, a client device, or other network device) that performs various functions of the seismic data analysis algorithms in accordance with various embodiments of the present disclosure. Each computing device 106 includes at least one processor circuit, for example, having a processor 2403 and a memory 2406, both of which are coupled to a local interface. To this end, each computing device 106 may be implemented using one or more circuits, one or more microprocessors, microcontrollers, application specific integrated circuits, dedicated hardware, digital signal processors, microcomputers, central processing units, field programmable gate arrays, programmable logic devices, state machines, or any combination thereof. The local interface 2409 may comprise, for example, a data bus with an accompanying address/control bus or other bus structure as can be appreciated. Each computing device 106 can include a display 2412 for rendering of generated graphics such as, e.g., a user interface 2300 and an input interface such, e.g., a keypad or touch screen to allow for user input. In addition, each computing device 2300 can include communication interfaces (not shown) that allows each computing device to communicatively couple with other communication devices. The communication interfaces may include one or more wireless connection(s) such as, e.g., Bluetooth or other radio frequency (RF) connection and/or one or more wired connection(s).

Stored in the memory 2406 are both data and several components that are executable by the processor. In particular, stored in the memory 2406 and executable by the processor are seismic tracking application(s) 118, a warning module 121, and/or other applications. Seismic tracking applications 118 can include applications that is collect and store data, process data analytics, communicate with other units, and provide raw and processed data to the visualization tool. For example, the seismic tracking application 118 can process the collected data associated with the corresponding sensor 106 and/or other sensors 106 in the network to track the footsteps or other activity of subjects in a given area. The warning module 121 can include applications that can generate alerts to notify other individuals and/or emergency entities in response to a detected event. It is understood that there may be other applications that are stored in the memory 2406 and are executable by the processor 2403 as can be appreciated. Where any component discussed herein is implemented in the form of software, any one of a number of programming languages may be employed such as, for example, C, C++, C#, Objective C, Java®, JavaScript®, Perl, PHP, Visual Basic®, Python®, Ruby, Delphi®, Flash®, LabVIEW® or other programming languages.

A number of software components are stored in the memory 2406 and are executable by the processor 2403. In this respect, the term "executable" means a program file that is in a form that can ultimately be run by the processor 2403.

Examples of executable programs may be, for example, a compiled program that can be translated into machine code in a format that can be loaded into a random access portion of the memory 2406 and run by the processor 2403, source code that may be expressed in proper format such as object code that is capable of being loaded into a random access portion of the memory 2406 and executed by the processor 2403, or source code that may be interpreted by another executable program to generate instructions in a random access portion of the memory 2406 to be executed by the processor 2403, etc. An executable program may be stored in any portion or component of the memory including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 2406 is defined herein as including both volatile and nonvolatile memory and data storage components. Volatile components are those that do not retain data values upon loss of power. Nonvolatile components are those that retain data upon a loss of power. Thus, the memory 2406 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 2403 may represent multiple processors and the memory 2406 may represent multiple memories that operate in parallel processing circuits, respectively. In such a case, the local interface 2409 may be an appropriate network that facilitates communication between any two of the multiple processors, between any processor and any of the memories, or between any two of the memories, etc. The local interface may comprise additional systems designed to coordinate this communication, including, for example, performing load balancing. The processor may be of electrical or of some other available construction.

Although the seismic tracking application(s) 118, the warning module 121, other applications and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits having appropriate logic gates, or other components, etc. Such technologies are generally well known by those skilled in the art and, consequently, are not described in detail herein.

Also, any logic or application described herein, including the seismic tracking application(s) 118, and the warning module 121, that comprises software or code can be embodied in any non-transitory computer-readable medium for use by or in connection with an instruction execution system such as, for example, a processor in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system. The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

In addition to the foregoing, the various embodiments of the present disclosure include, but are not limited to, the embodiments set for in the following clauses.

Clause 1. A monitoring system for monitoring activity in a predefined area, comprising: a network of sensor units arranged on a floor of the predefined area, individual sensor units of the network of sensor units comprising: a sensor; a computing device in data communication with the sensor; and at least one application executable in the computing device, wherein, when executed, the at least one application causes the computing device to at least: receive sensor data from the sensor, the sensor data comprising vibrations associated with one or more subjects moving on the floor; isolate footstep vibrations from the sensor data; communicate with at least one other sensor unit in the network of sensor units to obtain neighbor sensor data; and determine at least one of: a number of subjects moving in the predefined area, a trajectory for at least one subject, or a location of the at least one subject based at least in part on the footstep vibrations and the neighbor sensor data.

Clause 2. The system of clause 1, wherein the sensor comprises a seismometer.

Clause 3. The system of any one of clauses 1 or 2, wherein the network of sensor units are in data communication via a wireless network.

Clause 4. The system of any one of clauses 1 to 3, wherein isolating the footstep vibrations further comprises identifying one or more footstep signatures in time domain and frequency domain.

Clause 5. The system of any one of clauses 1 to 4, wherein determining the number of subjects moving in the predefined area further comprises clustering one or more footstep features from the sensor data with one or more footstep features from the neighbor sensor data.

Clause 6. The system of any one of clauses 1 to 5, wherein, when executed, the at least one application further causes the computing device to at least detect an event based at least in part on the footstep vibrations.

Clause 7. The system of clause 6, wherein the event comprises a fall of a particular subject.

Clause 8. The system of any one of clauses 6 or 7, wherein, when executed, the application further causes the computing device to at least generate an alert in response to the detected event.

Clause 9. The system of clause 8, wherein the alert is at least one of an auditory or visual alert.

Clause 10. The system of any one of clauses 8 or 9, wherein the computing device is in communication with a smart device configured to communicate with a third party, and generating the alert further comprises instructing the smart device to send a communication with the third party.

Clause 11. A method for monitoring activity in a predefined area, comprising: obtaining, via a computing device of a sensor unit positioned on a floor of the predefined area, sensor data from a sensor of the sensor unit, the sensor data being associated with one or more subjects moving on the floor; isolating, via the computing device, footstep vibrations from the sensor data based at least in part on wavelet denoising; determining, via the computing device, a location of a subject based at least in part on one or more signature features in the footstep vibrations and data received from at least one other sensor unit; and determining, via the computing device, a trajectory of the subject based at least in part on the location of the subject.

Clause 12. The method of clause 11, further comprising estimating, via the computing device, a number of occupants in the predefined area.

Clause 13. The method of any one of clauses 11 or 12, wherein the sensor comprises a seismometer.

Clause 14. The method of any one of clauses 11 to 13, further comprising generating, via the computing device, a user interface comprising at least one of: a trajectory tracking, a number of detected footsteps, a number of detected events, a fall down location, a number of detected falls, a time associated with a last detected event, or a time associated with a last detected fall.

Clause 15. The method of clause 14, further comprising: rendering, via the computing device, the user interface on a display associated with the computing device; and updating, via the computing device, the user interface periodically.

Clause 16. The method of any one of clauses 11 to 15, further comprising detecting, via the computing device, an event of the subject.

Clause 17. The method of clause 16, wherein the even comprises a fall down event.

Clause 18. The method of any one of clauses 16 or 17, wherein detecting the event is based at least in part on the footstep vibrations.

Clause 19. The method of any one of clauses 16 to 19, further comprising generating, via the computing device, an alert in response to the detected event.

Clause 20. The method of clause 19, wherein the computing device is in communication with a smart device configured to communicate with a third party, and generating the alert comprises instructing the smart device to send a communication with the third party.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

We claim:

1. A monitoring system for monitoring activity in a predefined area, comprising:
    a network of sensor units arranged on a floor of the predefined area, individual sensor units of the network of sensor units comprising:
        a vibration sensor configured to obtain horizontal vibrations and vertical vibrations;
        an amplifier;
        a computing device in data communication with the sensor; and
        at least one application executable in the computing device, wherein, when executed, the at least one application causes the computing device to at least:
            receive sensor data from the sensor, the sensor data comprising the horizontal vibrations and the vertical vibrations associated with one or more subjects moving on the floor;
            isolate footstep vibrations from background noise vibrations included in the sensor data based at least in part on a characterization of waveform properties in the sensor data;
            communicate with at least one other sensor unit in the network of sensor units to obtain neighbor sensor data; and
            determine at least one of: a number of subjects moving in the predefined area, a trajectory for at least one subject, or a location of the at least one subject based at least in part on the footstep vibrations and the neighbor sensor data.

2. The system of claim 1, wherein the vibration sensor comprises a seismometer.

3. The system of claim 1, wherein the network of sensor units are in data communication via a wireless network.

4. The system of claim 1, wherein isolating the footstep vibrations further comprises identifying one or more footstep signatures in time domain and frequency domain.

5. The system of claim 1, wherein determining the number of subjects moving in the predefined area further comprises clustering one or more footstep features from the sensor data with one or more footstep features from the neighbor sensor data.

6. The system of claim 1, wherein, when executed, the at least one application further causes the computing device to at least detect an event based at least in part on the footstep vibrations.

7. The system of claim 6, wherein the event comprises a fall of a particular subject.

8. The system of claim 6, wherein, when executed, the application further causes the computing device to at least generate an alert in response to the detected event.

9. The system of claim 8, wherein the alert is at least one of an auditory or visual alert.

10. The system of claim 8, wherein the computing device is in communication with a smart device configured to communicate with a third party, and generating the alert further comprises instructing the smart device to send a communication with the third party.

11. A method for monitoring activity in a predefined area, comprising:
obtaining, via a computing device of a sensor unit positioned on a floor of the predefined area, sensor data from a vibration sensor of the sensor unit, the sensor data being associated with one or more subjects moving on the floor;
isolating, via the computing device, footstep vibrations from background noise vibrations included in the sensor data based at least in part on wavelet denoising;
determining, via the computing device, a location of a subject based at least in part on one or more signature features in the footstep vibrations and data received from at least one other sensor unit; and
determining, via the computing device, a trajectory of the subject based at least in part on the location of the subject.

12. The method of claim 11, further comprising estimating, via the computing device, a number of occupants in the predefined area based at least in part on a learned data and an analysis of the sensor data.

13. The method of claim 11, wherein the sensor comprises a seismometer.

14. The method of claim 11, further comprising generating, via the computing device, a user interface comprising at least one of: a trajectory tracking, a number of detected footsteps, a number of detected events, a fall down location, a number of detected falls, a time associated with a last detected event, or a time associated with a last detected fall.

15. The method of claim 14, further comprising:
rendering, via the computing device, the user interface on a display associated with the computing device; and
updating, via the computing device, the user interface periodically.

16. The method of claim 11, further comprising detecting, via the computing device, an event of the subject.

17. The method of claim 16, wherein the event comprises a fall down event.

18. The method of claim 16, wherein detecting the event is based at least in part on the footstep vibrations.

19. The method of any one of claim 16, further comprising generating, via the computing device, an alert in response to the detected event.

20. The method of claim 19, wherein the computing device is in communication with a smart device configured to communicate with a third party, and generating the alert comprises instructing the smart device to send a communication with the third party.

* * * * *